(12) United States Patent
Ozaki et al.

(10) Patent No.: US 8,168,444 B2
(45) Date of Patent: May 1, 2012

(54) SUBSTRATE HAVING CHANNEL PORTION INCLUDING CHAMBERS, AND METHOD OF TRANSFERRING LIQUID BY USING THE SUBSTRATE

(75) Inventors: Nobuhiko Ozaki, Kanagawa (JP); Tomohiro Yamamoto, Osaka (JP)

(73) Assignee: Panasonic Corporation, Osaka (JP)

( * ) Notice: Subject to any disclaimer, the term of this patent is extended or adjusted under 35 U.S.C. 154(b) by 218 days.

(21) Appl. No.: 12/595,077

(22) PCT Filed: Apr. 4, 2008

(86) PCT No.: PCT/JP2008/000882
§ 371 (c)(1),
(2), (4) Date: Oct. 8, 2009

(87) PCT Pub. No.: WO2008/126404
PCT Pub. Date: Oct. 23, 2008

(65) Prior Publication Data
US 2010/0120166 A1    May 13, 2010

(30) Foreign Application Priority Data
Apr. 9, 2007  (JP) ................................. 2007-102090

(51) Int. Cl.
*B01L 3/00*  (2006.01)

(52) U.S. Cl. ........ 436/180; 436/174; 422/506; 422/503; 422/501; 422/500

(58) Field of Classification Search .................. 422/68.1, 422/72, 81, 64, 51, 502, 503, 506, 507; 436/180, 436/174
See application file for complete search history.

(56) References Cited

U.S. PATENT DOCUMENTS

| 2,668,134 | A  | * | 2/1954 | Horton ........................... 156/316 |
| 6,063,589 | A  | * | 5/2000 | Kellogg et al. .................. 435/24 |
| 6,212,417 | B1 |   | 4/2001 | Ikeda et al. |
| 2004/0018117 | A1 | * | 1/2004 | Desmond et al. ............... 422/64 |

FOREIGN PATENT DOCUMENTS

JP    2000-65778    3/2000

(Continued)

OTHER PUBLICATIONS

Vickers, Jonathan A. et al. "Generation of Hydrophilic Poly(dimethylsiloxane) for High-Performance Microchip Electrophoresis." Analytical Chemistry (2006) 78 7446-7452.*

(Continued)

*Primary Examiner* — Yelena G Gakh
*Assistant Examiner* — Christopher A Hixson
(74) *Attorney, Agent, or Firm* — Greenblum & Bernstein, P.L.C.

(57) ABSTRACT

A substrate having a channel portion in which a liquid transfers, wherein, even if the channel portion has no micro-channel interconnecting chambers, a liquid can transfer stepwise from one region to the next region according to the speed of rotation of the substrate. The substrate can be rotated about a rotation axis as the center, and has the channel portion including the chambers formed therein. The inner wall of each chamber has a first area including an area intersecting with a centrifugal direction from the center; and also has a second area placed at a position farther from the center than the first area, and including a surface intersecting with the centrifugal direction from the center. Further, the first area has a region for holding a droplet of a liquid provided; and also has a region where a contact with the droplet expands when the substrate is rotated, and that communicate with the second area.

9 Claims, 21 Drawing Sheets

FOREIGN PATENT DOCUMENTS

| | | |
|---|---|---|
| JP | 2000-514928 | 11/2000 |
| JP | 2001-503854 | 3/2001 |
| JP | 2001-327912 | 11/2001 |
| JP | 2002-503331 | 1/2002 |
| JP | 2005-345160 | 12/2005 |

OTHER PUBLICATIONS

English language Abstract of JP 2005-345160, Dec. 15, 2005.
English language Abstract of JP 2001-327912, Nov. 27, 2001.
English language Abstract of JP 2000-65778, Mar. 3, 2000.
English language Abstract of JP 2001-503854, Mar. 21, 2001.
English language Abstract of JP 2002-503331, Jan. 29, 2002.
English language Abstract of JP 2000-514928, Nov. 7, 2000.
Ekstrand et al., "Microfluidics in a Rotating CD", Micro Total Analysis Systems 2000, pp. 311-314.

* cited by examiner

STEP A

RETAIN DROPLETS 10 IN DROPLET
RETAINING AREA 16 IN FIRST INNER FACE 8

STEP B

ROTATE SUBSTRATE 2 AT THIRD ROTATION SPEED $RPM_3$

FIG.3

SUBSTRATE HAVING CHANNEL PORTION INCLUDING CHAMBERS, AND METHOD OF TRANSFERRING LIQUID BY USING THE SUBSTRATE

TECHNICAL FIELD

The present invention relates to a substrate having flow path part including chambers and a method of transferring liquid using the substrate.

BACKGROUND ART

In recent years, various health check chips have been developed. Most of these health check chips are a card device called "μ-TAS" (Micro Total Analysis System), which has a miniature flow path structure. A miniaturized flow path is very useful in that the required amount of a sample to extract from a living organism is small. Further, by making small entire apparatuses including the health check chip by miniaturizing the flow path, the apparatuses are applicable for use in POCT (Point of Care Test) that allows diagnosis in doctor's offices and households, not only in relatively large-scale hospitals.

In cases where a large amount of fluid flows, a pump is generally used as a liquid transferring means. However, in a miniature flow path that allows only a very small amount of fluid flows, it is not possible to pass over the dead volume in tube connected with the pump. Therefore, a pump is often not suitable for the liquid transfer means of a chip used in POCT.

Using centrifugal force for the source drive is suitable for a method liquid transfer in POCT (for example, Patent Documents 1 to 4). A method of liquid transfer by centrifugal force offers an advantage of not generating a dead volume and performing many processes at the same time in parallel.

For example, the substrate disclosed in Non-Patent Document 1 has a plurality of micro-chambers and micro-flow paths. In the substrate, the width of the micro-flow path connecting between the micro-chambers is adjusted. To be more specific, in a range between about 10 and 100 μm, micro-flow path that are more distant from the center of rotation has a narrower width. By this means, micro-flow path that is more distant from the axis of rotation generate greater capillary force. Liquid in a miniature chamber in which liquid transfer is blocked by the capillary force generated in the micro-flow path, is transferred to the neighboring micro-chamber in the centrifugal direction by the centrifugal force generated by the rotation of the substrate. The centrifugal force required to transfer liquid in a micro-chamber corresponds to the capillary force generated in the micro-flow paths. As described above, the micro-flow path is designed to generate greater capillary force as distant from the axis of rotation. Therefore, without increasing the speed of rotation, it is not possible to transfer liquid from one micro-chamber to neighboring micro-chamber in the centrifugal direction. That results in realizing stepwise liquid transfer.

Patent Document 1: Japanese Patent Application Laid-Open No. 2000-065778
Patent Document 2: Japanese Translation of a PCT Application Laid-Open No. 2001-503854
Patent Document 3: Japanese Translation of a PCT Application Laid-Open No. 2002-503331
Patent Document 4: Japanese Translation of a PCT Application Laid-Open No. 2000-514928
Non-Patent Document 1: Micro Total Analysis Systems 2000, pp. 311-314

DISCLOSURE OF INVENTION

Problems to be Solved by the Invention

However, the liquid transfer in multi-chambers substrate disclosed in Patent Document 1, there are two factors to limit the width of flow path connecting between chambers.

The first limiting factor is that the width of the flow path depending on position of a chamber (i.e. distance from the center of rotation) has to be equal or less than depth of the flow path. The present inventors have actually made a substrate including flat flow paths that has greater widths than the depths, despite the first limiting factor. The number of chamber stages was three, the inner flow path width was 750 μm, the outer flow path width was 300 μm, and both of the flow path depths were 15 μm. Multistage liquid transfer was not realized using the made substrate. That is, upon applying the first rotation speed to the substrate, outflow liquid from the innermost chamber did not come to a stop in the next chamber and was transferred to the outermost chamber all at once.

One possible reason that the desired liquid transfer operation was not made possible is that the widths of the flow paths (750 μm and 300 μm) were made greater than the depths of the flow paths (15 μm). The pressure applied to the cross-section of the flow path by capillary force is in proportion to the perimeter thereof, and in reverse proportion to the cross-sectional area thereof. Therefore, to increase the pressure applied by capillary force significantly, the increasing amount of the pressure by increasing in the perimeter needs to be greater than the decreasing amount of the pressure change by increasing in the cross-sectional area. For that reason, among a width and a depth of cross-sectional of flow path, the shortest dimension, that is width, needs to be made small.

The second limiting factor is that a flow path that is more distant from the axis of rotation has narrower width. The flow path having a width or depth between about 10 and 100 μm is generally made using photolithography technology. It is possible to change the width of flow path by changing the line width of the photo-mask. Although the width of flow path needs to be made smaller as the number of stages of chambers increases, there is a limit to be made. For example, it is not possible with the state of the art to make a width about 1 μm or less, that is, to make the aspect ratio 100 or more in flow path having a depth of 100 μm. Further, the depth of flow path is determined depending on etching depth, and therefore it is difficult to form local area having a specific depth, which corresponds to the flow path.

For the above reasons, the process of producing a substrate involves a heavy load, in which adjusting a cross-sectional area of a micro-flow path is formed, and by which stepwise liquid transfer is realized. Furthermore, there are cases where the substrate that realizes multistage liquid transfer cannot be produced.

It is therefore an object of the present invention to provide a substrate, which has flow path part in which liquid transfers, and which allows liquid to transfer from one area to the next area stepwise according to the rotation speed of substrate, even when there is not a micro-flow path connecting between chambers in the flow path part. In the substrate of the present invention, liquid transfers from one area to the next area in one chamber of the flow path part, or transfers from one chamber to other chamber without going through a micro-flow path in the flow path part. Further, it is another object of the present invention to provide a method of producing at a light load a substrate which has flow path part in which a liquid transfers, the step of forming a micro-flow path is not necessary for the method.

Means for Solving the Problem

That is, the first aspect of the present invention relates to the following substrate. [1] A substrate that is rotatable about a rotating axis and that has a flow path part including a chamber formed inside the substrate, wherein: an interior wall of the chamber adopts a configuration including: a first inner face that has a plane intersecting with a centrifugal direction from the rotating axis; and a second inner face that has a plane which is placed in a location farther from the rotating axis than the first inner face and which intersects with the centrifugal direction from the rotating axis; the first inner face has an area that retains droplet of liquid supplied, and an area that allows expansion of a contact area of the retained droplet by rotation of the substrate and communicates with the second inner face.

The second aspect of the present invention relates to the following method of transferring a liquid inside the substrate. [2] A method of transferring liquid in a chamber formed inside the substrate according to [1], includes the steps of: retaining droplet of liquid on a droplet retaining area in a first inner face; and transferring the liquid to the second inner face such that the substrate rotates about a rotating axis to spread a contact area of retained droplet.

The third aspect of the present invention relates to the following apparatus. [3] A liquid transfer apparatus adopts a configuration including: the substrate according to [1]; and a rotation drive part that moves the substrate around a center of rotation.

Advantageous Effects of Invention

The present invention allows liquid to transfer stepwise in flow path part formed inside a substrate. By allowing liquid to transfer stepwise, it is possible to give the substrate various functions. These various functions include allowing a dried reagent supported in a chamber to react with a liquid in a predetermined period, and allowing a plurality of dried reagents respectively supported in a plurality of areas to react with a liquid in a predetermined order. Furthermore, the substrate of the present invention does not require micro-flow path connecting between chambers, and therefore involves a lighter load of the producing process, thereby improving the feasibility of producing the substrate.

BRIEF DESCRIPTION OF DRAWINGS

FIG. 3 is a flow chart showing a method of liquid transfer using the substrate according to Embodiment 1;

BEST MODE FOR CARRYING OUT THE INVENTION

Figure 1:
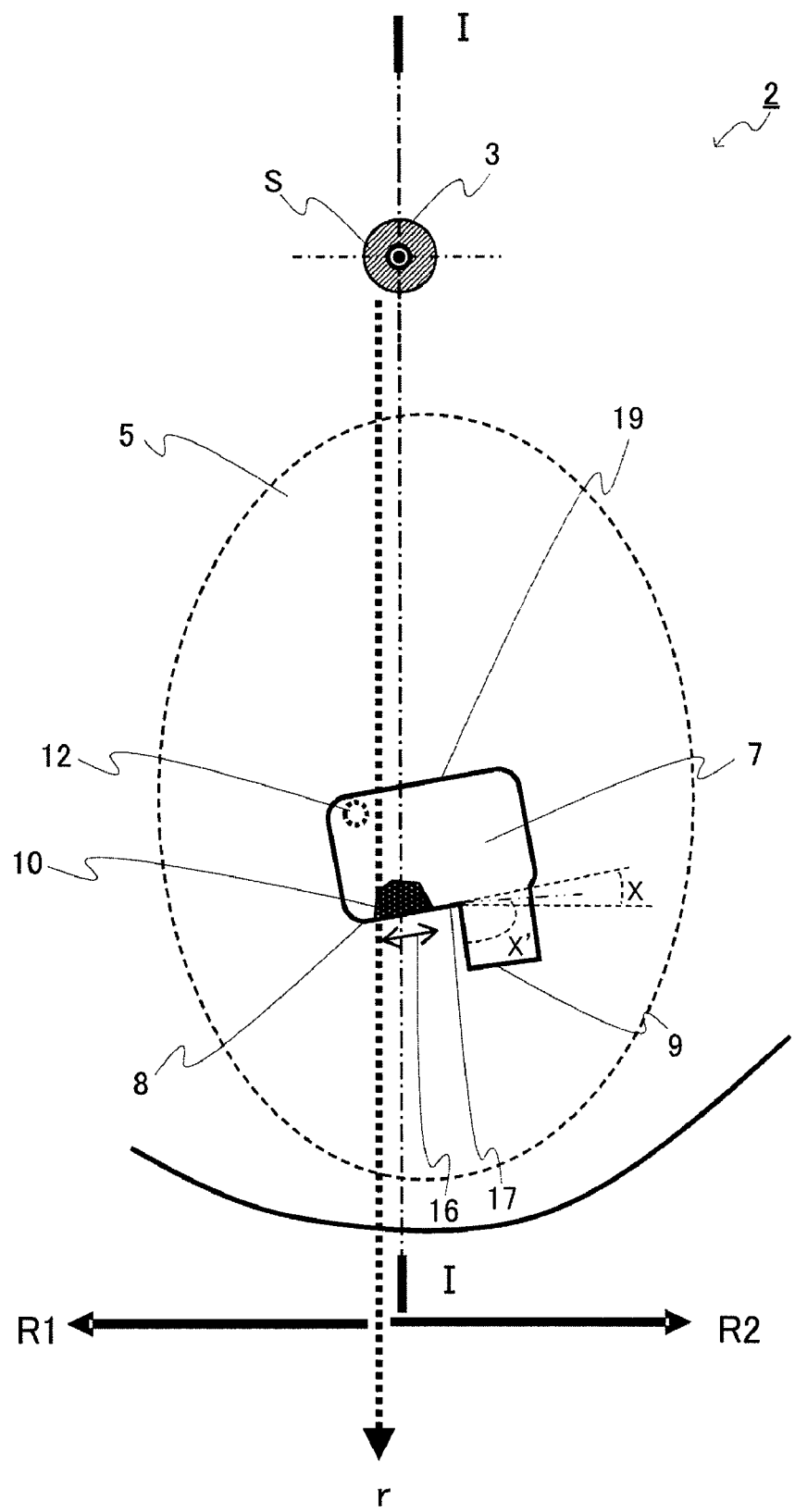
FIG. 1 is a partial cross-sectional view of the substrate according to Embodiment 1.

1. The Substrate of the Present Invention

The substrate of the present invention is rotatable about the rotating axis, which is the center of rotation. The direction of rotation is perpendicular to an imaginary line intersecting at right angles with the axis of rotation, and is sharing the same plane with this imaginary line. For example, when the substrate is fixed to the rotating shaft, the substrate is rotatable in the tangential directions perpendicular to the radial direction of the rotating axis. The direction of rotation may be clockwise or counterclockwise with respect to the axis of rotation in a plan view.

The substrate may have an arbitrary outer shape, for example, a disc shape, cube, a rectangular parallelepiped, polygon such as pentagon and star shape. The size of the substrate may be set arbitrarily in dimensions that can accommodate the flow path part. A representative outer shape of the substrate is set, for example, between about 10 and 150 mm (the length in a plan view). Further, the thickness of the substrate is preferably between about 0.1 and 30 mm.

The substrate of the present invention has flow path part including chambers therein. One or more flow path parts are included in the substrate. Further, one or more chambers are included in each flow path part.

As described above, one or more chambers are included in each flow path formed in the substrate. At least one of chambers has an interior wall including a first inner face and a second inner face. Further, each chamber may have an injection inlet through which liquid can be injected into the chamber. The shape of the injection inlet is not limited to a circle, and may be other shapes such as an oval and a polygon.

The first inner face, which is a part of interior wall of a chamber, includes a plane that intersects with centrifugal direction from the axis of rotation of the substrate. The intersecting plane may be flat or curved. "The angle of intersecting" is not particularly limited here, and preferably between about −34° and 34° because a droplet has to be retained on the plane upon rotating the substrate. Here, "the angle of intersecting" refers to an angle formed between a plane perpendicular to the centrifugal direction and the first inner face (see angle X in FIG. 1).

The second inner face, which is a part of interior wall of the chamber having the first inner face, refers to a plane that intersects with centrifugal direction from the axis of rotation of the substrate. However, the second inner face is preferably located at a position that is more distant from the axis of rotation than the first inner face. Here, "the angle of intersecting" of the plane intersecting with the centrifugal direction is not particularly limited.

The first inner face included in the substrate of the present invention has: an area on which liquid supplied to a chamber is retained in droplet (referred to as the "retaining area"); and an area that allows the expansion of the contact area of the retained liquid droplet when the droplet is subject to centrifugal force by rotation of the substrate (referred to as the "expansion area"). That is, the expansion area is placed around the retaining area. Further, the expansion area has a feature of communicating with the second inner face. The angle between a plane that communicates with the second inner face from periphery of the expansion area and a plane intersecting at right angles with centrifugal direction is 9° or more, and preferably +34° or more (see angle X' in FIG. 1). A positive intersecting angle is defined as an angle between the plane intersecting at right angles with centrifugal direction and the plane extending in centrifugal direction which communicates the expansion area with the second inner face. By adjusting this angle of intersecting, droplet having passed the periphery of "expansion area" is made a slide on the second inner face.

The retaining area included in the first inner face is preferably hydrophobic. Since the retaining area is hydrophobic, liquid is retained in droplet easily on the retaining area, and therefore it is possible to prevent the supplied liquid from wetting the entire first inner face.

Further, by making the retaining area more hydrophobic, it is possible to make greater the contact angle of droplet with respect to the retaining area. By making greater the contact angle of droplet, the area where droplet is retained and the contacting area with droplet decrease. That is, it is possible to reduce the surface tension acting on the retained droplet. For this purpose, coating treatment may be applied to retaining area to improve hydrophobic.

As described later, by expanding a contact area of droplet retained on the retained area by centrifugal force, the liquid is transferred to the second inner face. When the surface tension is small, less centrifugal force allows the contact area of droplet to expand. Therefore, small surface tension makes it possible to transfer droplet at lower rotation speed. By transferring the liquid at low rotation speed, stepwise transfer can be realized more definitely by controlling the rotation speed.

Therefore, a static contact angle of droplet on the retaining area is preferably between 30° and 118°, more preferably, between 60° and 90°, representatively 86°. When the static contact angle is less than 30°, the retaining area is hydrophilic and droplet expands too much on the retaining area, therefore it is not preferable. On the other hand, when the static contact angle is between 120° and 160°, the retaining area is too water-repellent, and the shape of droplet retained becomes close to a sphere. The sphere droplet retained on the retaining area is difficult to expand even when the substrate rotates. Further, when the static contact angle is 160°, the droplet falls in the second inner face easily, and therefore, the acceptable angle of intersecting (i.e. the angle formed between the face of retaining area and the plane perpendicular to a centrifugal direction) needs to make smaller, between 4° to 7°. In this way, the shape and orientation of the first inner face are limited.

One of examples is that, when droplet is retained on the retaining area at a static contact angle of 86°, the droplet can be retained on the retaining area having the intersecting angle in a range between −10° and 10°.

To improve hydrophobicity in retaining area and to make larger the angle of intersecting, the retaining area may be subject to coating treatment. For example, if droplet is retained on a first inner face that is not subject to coating treatment at a contact angle of 76°, the droplet is retained on a first inner face that is coated with an epoxy resin at the contact angle of 92°. By the coating with the epoxy resin, the droplet can be retained on the first inner face when the intersecting angle between the first inner face and the direction in centrifugal direction may be adjusted in the range between −34° and 34°. When the retaining area is coated with a fluorine-containing coating agent. the droplet is retained on the first inner face at a contact angle of 102°. By the coating with the fluorine-containing coating agent, the droplet can be retained on the first inner face when the intersecting angle between the first inner face and the centrifugal direction may be adjusted in the range between −12° and 12°. When the retaining area is coated with a silicon water repellent, the droplet is retained on the first inner face at a contact angle between 85 and 95°. By the coating with the silicon water repellent, the droplet can be retained on the first inner face when the intersecting angle between the first inner face and the centrifugal direction may be adjusted in the range between −9° and 9°. Further, when the retaining area is coated with an acrylic urethane water repellent, the droplet is retained on the first inner face at a contact angle of 70°. By the coating with the acrylic urethane water repellent, the droplet can be retained on the first inner face when the intersecting angle between the first inner face and the centrifugal direction is adjusted in the range between −30° and 30°. In this way, the intersecting angle between the first inner face and the centrifugal direction can be changed depending on the hydrophobicity of the first inner face and by coating treatment to the first inner face.

As described above, retaining area in the first inner face is preferably hydrophobic, and the entire first inner face may be hydrophobic, and furthermore, all interior walls in a chamber may be hydrophobic. That improves the productivity of the substrate. Further, by making the entire first inner face hydrophobic, liquid droplet is not only able to be retained more reliably, and can be retained on the entire first inner face including the expansion area. Therefore, when the entire first inner face is hydrophobic, in order to transfer a predetermined amount of liquid from the first inner face to the second inner face, it is necessary to continue rotation drive at the threshold rotation speed or above. By controlling the duration of the rotation drive, it is possible to transfer more accurately predetermined amount of liquid from the first inner face to the second inner face in a chamber. The controlling transfer of liquid by adjusting the duration of the rotation drive is valid in the case where the liquid is transferred to be subjected to a reaction in other area on a predetermined timing.

Not only in the first inner face in a chamber, all interior walls of flow path part (including other chambers and connecting parts that connect between chambers) may be hydrophobic. By forming all faces of flow path part from a hydrophobic material or by applying hydrophobic treatment to all flow path parts, productivity improves. Further, the entire substrate may be hydrophobic. By forming the entire substrate from a hydrophobic material or by applying hydrophobic treatment to the entire substrate, productivity further improves.

The cross-section area of the retaining area is determined according to the amount of droplet retained. It is preferable that the amount of droplet retained is approximately between about 0.1 and 10 μL. Liquid contacts the retaining area in the form of droplet with a certain cross sectional area. There are two requirements to be met to form droplet on the retaining area on the bottom face of a chamber, and to form no droplet on the side face of a chamber. The first one is, as described above, to make the retaining area hydrophobic. The second one is to set up the retaining area larger than the cross sectional area of contacting droplet. To be more specific, when the amount of liquid retained is between 0.1 and 10 μL, the width of the retaining area in a plan view is preferably between 0.5 and 5 mm. In particular, when the retained amount of liquid is between 0.1 and 2 μL, the width of the retaining area in a plan view is preferably between 0.75 and 2.4 mm. The depth of the retaining area is preferably between 0.1 and 4 mm, and, more preferably, between 0.2 and 1 mm.

The clearance distance from the retaining area to upper ceiling surface 19 (see FIG. 1) of the chamber along the centripetal direction is set longer than the height of retained droplet. To be more specific, when the amount of liquid retained is between 0.1 and 2 μL, the liquid droplet does not contact upper ceiling surface when the clearance distance is 0.8 mm or more, and therefore, the clearance distance is preferably 2 mm or more, and more preferably 4 mm or more for definitely preventing the droplet from contacting with the upper ceiling surface.

Meanwhile, the expansion area included in the first inner face is placed around the retaining area. As described later, the contact area of droplet retained on the retaining area is spread by centrifugal force by rotations of the substrate. At that time, droplet expands into the expansion area by the spread. The width of expansion area extended from the retaining area is preferably between 0.3 and 13 mm in a plan view, and, more preferably, between 0.5 and 2.5 mm. If the width of the expansion area is 0.3 mm or less, the droplet cannot be retained stably on the retaining area. A volume of 10 μL droplet is retained with a circular cross section of a 3.3 mm diameter. Even though the substrate rotates at a rotation speed of 3000 rpm, the width of a volume of 10 μL droplet does not spread beyond 28 mm. The volume of droplet retained is usually 10 μL or less, and therefore, it normally suffices that the width of expansion area between the circumference of retaining area and the circumference of expansion area is of a 12.3 mm.

If the expansion area is made greater, the expansion of the contact area of droplet has to be made greater in order to transfer liquid to the second inner face. Therefore, the rotation speed of the substrate for transfer has to be increased to increase centrifugal force. Therefore the size of the expansion area may be set according to the rotation speed for transfer.

The second inner face is placed more distant from the center of rotation of the substrate than the first inner face, and communicates with the expansion area of the first inner face. Therefore, when liquid droplet retained on the retaining area is spread to pass beyond the expansion area by centrifugal force, the liquid is transferred to the second inner face.

A retaining area and expansion area may be provided also in the second inner face. In that case, it is preferable that a third inner face is located. The third inner face, which is part of interior wall of the chamber, includes a plane that intersects with the centrifugal direction from the axis of rotation. Also, the third inner face is placed more distant from the center of rotation of the substrate than the second inner face, and preferably communicates with the expansion area for droplet on the second inner face. Similarly, a fourth inner face, a fifth inner face, ... and a n-th inner face may be provided.

The flow path part formed in the substrate of the present invention may have two or more chambers including the first chamber and a second chamber, and a connecting part that communicates with the first chamber and the second chamber. The first chamber is preferably placed closer the center of rotation of the substrate than the second chamber. The first chamber is spatially closed except for the injection inlet. The second chamber includes the above-described first inner face and second inner face.

The liquid in the first chamber injected from outside of the substrate through the injection inlet is preferably supplied to the second chamber by rotation of the substrate (described later in detail). Therefore, it is preferable that the connecting part that communicates with the first chamber and the second chamber is connected with a part of the first chamber, the part which is distant from the center of rotation, so as to adequately supply liquid in the first chamber to the second chamber by centrifugal force.

The liquid supplied from the first chamber to the second chamber is retained on the retaining area in the first inner face of the second chamber. Therefore, it is preferable that the connecting part is adjusted such that the connecting part is directed toward the retaining area of the first inner face.

A cross section of the connecting part that communicates with the first chamber and the second chamber can be larger than that of so-called "micro-flow path," and the substrate having no "micro-flow path" can be produced easily.

For example, the width of connecting part 15 (see FIG. 5) is preferably between about 100 and 2000 μm, more preferably, between about 300 and 1000 μm. Further, the depth of connecting part 15 is preferably shallower than the depths of supply source chamber 6 and supply destination chamber 7. For example, when the connecting part 15 has a width of about 300 and 1000 μm, it is preferable that the connecting part 15 has a depth of approximately between 50 and 300 and, more preferably, a depth of approximately between 100 and 200 μm.

One or more flow path parts can be provided in the substrate. By providing two or more flow path parts in one substrate in an integrated manner, it is possible to transfer liquid in each chamber in flow path part from the first inner face to the second inner face at the same time by a single rotation driving of the substrate (described later). By integrated flow path parts in one substrate, the parallel processing for transferring a plurality kind of liquids is realized, and consequently, it is possible to process a great number of samples in a short time.

Further, every flow path part has different chambers and connecting parts, so that it is possible to control liquid transfer individually at different rotation speeds on a per flow path part basis. Consequently, it is possible to perform a plurality of types of measurement sequences with one substrate. For example, multiple measuring, which includes a glucose measuring in a one-step reaction in flow path part 1 and a cholesterol measuring in a three-step reaction in flow path part 2, is realized.

Further, the cost of testing one sample can be lowered by forming a number of flow path parts in one substrate in view of the manufacturing cost for the substrates.

The substrate of the present invention may have a central axis member that works as the axis of rotation. By having a member of the central shaft, the substrate itself can rotate without a mechanism to mount on the rotation drive member, so that the liquid transfer apparatus (described later) becomes more convenient. From the aspect of the manufacturing cost for the substrate, it is effective in lowering the cost of testing sample.

2. The Liquid Transfer Method of the Present Invention

The method of transferring liquid according to the present invention (also referred to as the "liquid transfer method") refers to the method of transferring a solution stepwise from one area to another area in chamber in flow path part formed inside the substrate of the present invention. The liquid transfer method of the present invention includes a step of rotating the substrate of the present invention.

The first of the liquid transfer method of the present invention prepares a substrate of the present invention and includes: (1) retaining a droplet on a retaining area in the first inner face of a chamber: and (2) transferring the liquid to the second inner face such that the substrate rotates about a rotating axis to spread a contact area of the droplet retained on the retaining area.

(1) The Step of Retaining Droplet

The liquid supplied in a chamber contacts the retaining area in the first inner face, and cohesive force works to maintain the droplet shape of the liquid. Therefore the liquid is retained in the form of droplet on the retaining area of the first inner face, and the droplet is retained on the retaining area at a contact angle.

The contact angle of the droplet with respect to the retaining area in the first inner face is determined by the resultant force of surface tensions that work along the centripetal direction (that is, the direction to the axis of rotation). Also, the size of an area where droplet is retained is determined by the resultant force of the surface tensions.

The liquid is supplied to a chamber using arbitrary methods. For example, liquid may be injected from outside of the substrate to a chamber through the injection inlet formed on the chamber, and may be provided from another chamber communicated via a connecting part.

(2) The Step of Transferring Liquid to the Second Inner Face

When the substrate rotates about the rotating axis, centrifugal force along the centrifugal direction (i.e. the direction to away from the center of rotation) is supplied to the liquid droplet retained on the retaining area in the first inner face. The liquid droplet, to which the centrifugal force supplied, receives the resultant force of surface tensions along the direction of centripetal direction (i.e. the direction to the center of rotation). As a result, the droplet shape is maintained. The resultant force of surface tensions balances with the centrifugal force, so that the contact area of liquid droplet spreads, and therefore the contact circumference of droplet spreads. Therefore, the droplet spread out over the "expansion area" around the retaining area.

Upon increasing the rotation speed to increase centrifugal force, the resultant force of surface tensions increase more, so that the contact circumference of the droplet is longer. When the rotation speed reaches a certain speed, the droplet try to spread beyond the expansion area to let the liquid flow to the second inner face communicating with the expansion area. The rotation speed of the substrate when liquid flows to the second inner face is referred to as the "transfer rotation speed."

The transfer rotation speed is preferably determined in the range of 600 to 10000 rpm, and, more preferably, designed in the range of 1000 to 3000 rpm. Further, the transfer rotation speed can be set on an arbitrary basis depending on the size of the expansion area.

In this way, by applying the transfer rotation speed, it is possible to transfer liquid from the first inner face to the second inner face. Therefore, by controlling the rotation speed of the substrate, it is possible to adjust the timing on which the droplet transfers, thereby realizing stepwise liquid transfer.

In the case where the second inner face has a retaining area and expansion area, and a third inner face is placed more distant from the center of rotation of the substrate than the second inner face, by increasing the rotation speed of the substrate further, it is possible to transfer liquid from the second inner face to the third inner face. In this way, stepwise liquid transfer in accordance with rotation speed is realized without going through micro-flow paths.

As described above, the retaining area in the first inner face is hydrophobic. Therefore, it is possible to prevent liquid in contact with the first inner face from wetting the entire first inner face (including the expansion area) without being subjected to centrifugal force. Therefore, the transfer liquid by controlling rotation speed is definitely realized. Further, by making greater the contact angle of droplet to the retaining area, it is possible to make the droplet retaining area small and the contact circumference of droplet short. That is, the surface tension which the droplet receives decreases, and therefore it is possible to expand the contact area of the droplet by smaller centrifugal force, thereby transferring the liquid at a lower rotation speed. By transferring liquid at a lower rotation speed, it is possible to increase the number of stages for liquid transfer, thereby enabling more complex transfer control.

As described above, the flow path part of the substrate of the present invention may have the first chamber and second chamber, and the connecting part that communicates both chambers. The second liquid transfer method of the present invention prepares a substrate having the first chamber and second chamber, and includes steps of: A) retaining droplet of liquid on an retaining area in the first inner face of the second chamber such that the substrate rotates about a rotating axis at a first rotation speed, to allow the liquid injected into a first chamber to flow into the second chamber; and B) transferring the liquid to a second inner face such that the substrate rotates about the rotating axis at a second rotation speed, the second rotation speed which is faster than the first rotation speed to expand a contact area of the retained droplet.

When the substrate rotates at an initial rotation speed lower than the first rotation speed, liquid injected in the first chamber is subjected to centrifugal force and pressed against the wall of the first chamber along the centrifugal direction. When a cross-sectional area of the connecting part is set adequately, liquid is not led to the second chamber at the initial rotation speed.

When the rotation speed of the substrate increases to the first rotation speed, liquid injected in the first chamber intrudes into the connecting part to flow into the second chamber. The liquid flowing into the second chamber contacts the first inner face having a plane that intersects with the centrifugal direction, to be retained in droplet on the retaining area in the first inner face. A part of the first inner face intersects with centrifugal direction, and therefore receives the liquid flowing into the second chamber thorough the connecting part and prevents an excess motion of the liquid.

By rotating the substrate, it is possible to supply liquid from the first chamber to the first inner face of the second chamber and place the droplet at accurate position. The liquid in the first chamber injected through the injection inlet is retained on an end part of the connecting part by capillary force. The capillary force then is called "the first capillary force." By rotating the substrate at the first rotation speed, the first centrifugal force works on the liquid retained on the end part along the centrifugal direction (i.e. the direction away from the center of rotation). The volume among the total liquid subjected to the first centrifugal force is a cubic content having a bottom area corresponding to the end part and a height corresponding to the distance to a surface of the liquid from the end part. When the first centrifugal force exceeds the first capillary force, the liquid in the first chamber flows into the connecting part to be led to the first inner face of the second chamber.

Contact circumference of droplet retained on the retaining area in the first inner face is determined such that the resultant force of surface tensions along the centripetal direction is balanced with the centrifugal force along the centrifugal direction.

After droplet is retained on the retaining area in the first inner face, liquid may be transferred from the first inner face to the second inner face as in the same way as the above-described first liquid transfer method of the present invention.

By the second liquid transfer method of the present invention, it is possible to provide liquid on the first inner face at predetermined timing, thereby being applicable to full automation of liquid transfer.

The amount of liquid transferred by the liquid transfer methods of the present invention may be little, preferably, for example, between 0.1 and 10 μL.

3 The Liquid Transfer Apparatus of the Present Invention

The apparatus of the present invention has: a substrate of the present invention; and a rotation drive part that can rotate the substrate around the center of the rotation. By rotating the substrate by the rotation drive part, the above-described liquid transfer method is realized.

The rotation drive part included in the apparatus preferably has a motor that rotates the substrate around the center of rotation and a speed control section that gives speed characteristics to the motor, thereby applying predetermined rotation to the substrate and allowing multistage liquid transfer in flow path part in the substrate.

Examples of motor included in the rotation drive part include, for example, a DC motor, DC brushless motor, AC motor and step motor. A step motor is preferable because hard rotating and hard braking of the substrate are easily realized only by applying driving signals from outside. Further, a DC motor does not particularly require a driving circuit (described later). In the case where a DC brushless motor which includes the driving circuit (described later) having a function of applying reverse rotation voltage is employed, a faster hard braking is realized.

The rotation drive part may further have a driving speed detector that detects the rotation speed of the substrate during rotation; and have a driving speed correction section that corrects the speed characteristics given to the motor by the speed control section based on the rotation speed detected by the driving speed detector. The rotation drive part rotates the substrate while the actual rotation speed is fed back to correct speed characteristics, so that the amount of liquid transfer is stabilized and the repeatability of the amount of liquid transfer improves.

Next, embodiments of the present invention will be described in detail with reference to the accompanying drawings.

Embodiment 1

FIGS. 1 to 4 show substrate 2 according to Embodiment 1. As shown in FIG. 1, substrate 2 of Embodiment 1 can be rotated together with rotating shaft 3. As arrows R1 and R2 shown in FIG. 1, the substrate rotates in directions to intersect with radial direction "r" from rotating axis 3 at right angles. The direction of rotation defined as directions that are perpendicular to a imaginary line intersecting at a right angle with axis S of rotating axis 3 and that share the same plane with the imaginary line. Substrate 2 is rotatable clockwise R1 or counterclockwise R2 in a plan view.

Substrate 2 has flow path part 5. Referring to FIGS. 1 and 2, flow path part 5 has supply destination chamber 7. Supply destination chamber 7 is a chamber in which liquid 10, which is the target of transfer, is accommodated. Supply destination chamber 7 is formed inside substrate 2, and may be spatially closed.

The interior wall of supply destination chamber 7 has first inner face 8 and second inner face 9. First inner face 8 has retaining area 16 on which a droplet of liquid 10 is retained, and expansion area 17 that allows the droplet retained on retained area 16 to expand by rotation of the substrate 2. First inner face 8 has a plane that intersects with the centrifugal direction, that is, in FIG. 1 the plane that is substantially orthogonal to the centrifugal direction is provided. The arrangement of first inner face 8 is adjusted so that the resultant force of surface tensions, which the droplet placed on retaining area 16 and expansion area 17 receives, is not directed to the centrifugal direction away from the rotating axis. In this way, the first inner face 8 can be arranged with high degree of freedom, which is preferable from the aspect of the productivity of the substrate.

Meanwhile, second inner face 9 is located more distant from axis S than first inner face 8.

Supply destination chamber 7 has a shape of connecting two substantially rectangular shapes in a plan view. Air opening having a circular cross-section may be formed on supply destination chamber 7, and communicates the inside of chamber 7 with the outside of substrate 2. Air opening 12 may be used as the injection inlet for providing liquid on first inner face 8.

Air opening 12 is located in a position closer to axis S than retaining area 16 in the first inner face. That prevents liquid in the chamber 7 from spattering through air opening 12 by rotation of substrate 2. An opening to introduce liquid 10 on liquid retaining area 16 may be provided independently.

The cross-sectional shape of air opening 12 is not limited to a circle, and other shapes such as an oval and polygon may be applicable. Further, air opening 12 may be provided by way of forming a part of the wall of supply destination chamber 7 from air-transmissible material that is not liquid-transmissible. In this case, leakage of liquid 10 needs not to be taken into account when substrate 2 rotates, and therefore, it is possible to make the area of air opening 12 comparatively large.

The droplet volume of liquid 10 retained on retaining area 16 is preferably between 0.1 and 10 μL.

Retaining area 16 in first inner face 8 of supply destination chamber 7 is preferably hydrophobic. Since retaining area 16 is hydrophobic. by surface tension that the liquid retained on the droplet retaining area 16 in first inner face 8 receives, liquid can be present in the form of droplet. By increasing the hydrophobicity of retaining area 16, it is possible to make the contact angle of droplet greater. By making the contact angle of droplet greater, it is possible to make the circumference of the droplet on the retaining area smaller. By making the circumference of the droplet on the retaining area smaller, the surface tension the droplet receives smaller, so that droplet can spread by smaller centrifugal force. Consequently, it is possible to realize the transfer of liquid at a lower rotation speed.

Meanwhile, expansion area 17 in first inner face 8 may be hydrophobic or hydrophilic. In cases where expansion area 17 is hydrophilic, when droplet retained on retaining area 16 spread in expansion area 17, the droplet further spread by wetting effect as if droplet wets the expansion area.

To make a part hydrophobic, this part may be formed from hydrophobic materials or hydrophobic treatment may be conducted to this part. Examples of hydrophobic materials include: semiconductor materials represented by, for example, a single crystal silicon, amorphous silicon, silicon carbide, silicon oxide and silicon nitride; an inorganic insulation material selected from a group of alumina, sapphire, forsterite, silicon carbide, silicon oxide and silicon nitride; and an organic material selected from a group of polyethylene, ethylene, polypropylene, polyisobutylene, polyethylene terephthalate (PET), unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate (PC), polyamide, phenolic resin, urea resin, epoxy resin, melamine resin, styrene-acrylonitrile copolymer, acrylonitrile butadiene styrene copolymer, silicone resin, polyphenylene oxide and polysulphone. The suitable materials include PET or PC. Examples of hydrophobic treatment include applying a fluorine-containing resin coating agent, silicone-containing resin coating agent, acrylic urethane-containing resin coating agent, epoxy contained resin coating agent and so on. Preferably, a fluorine-containing resin coating agent is used.

The First Example of Layered Structure of Substrate 2

Figure 2A:
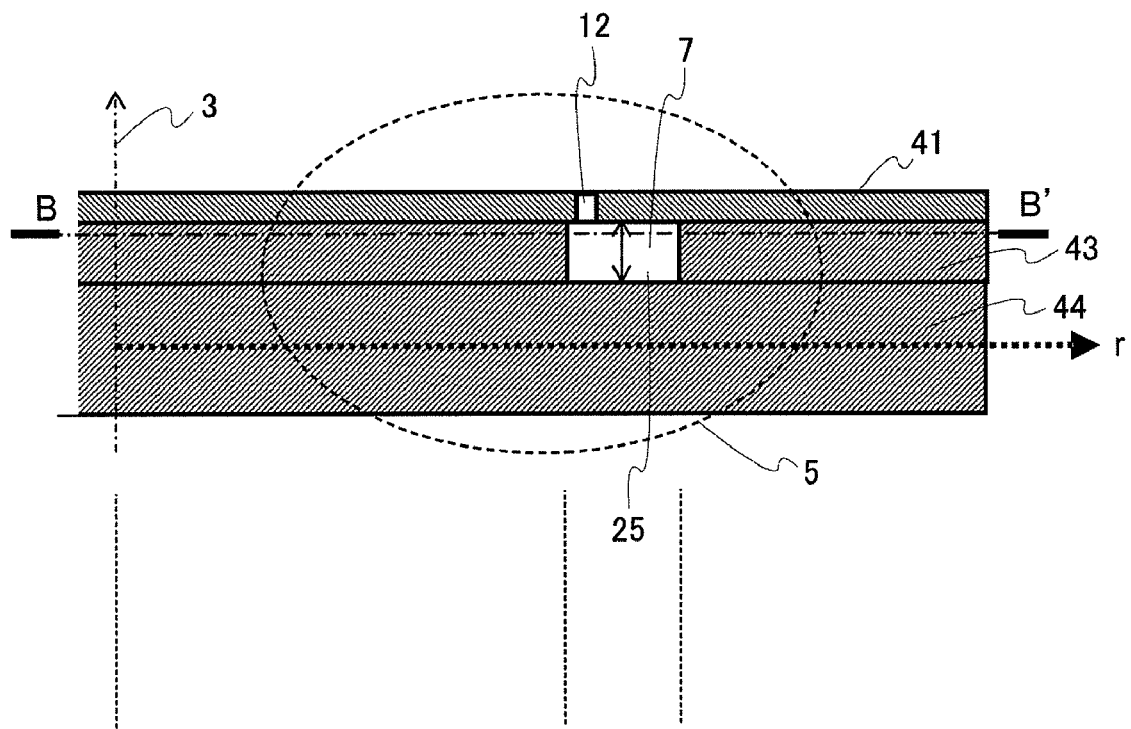
FIG. 2A is a partial cross-sectional view along I-I line in FIG. 1.
Figure 2B:
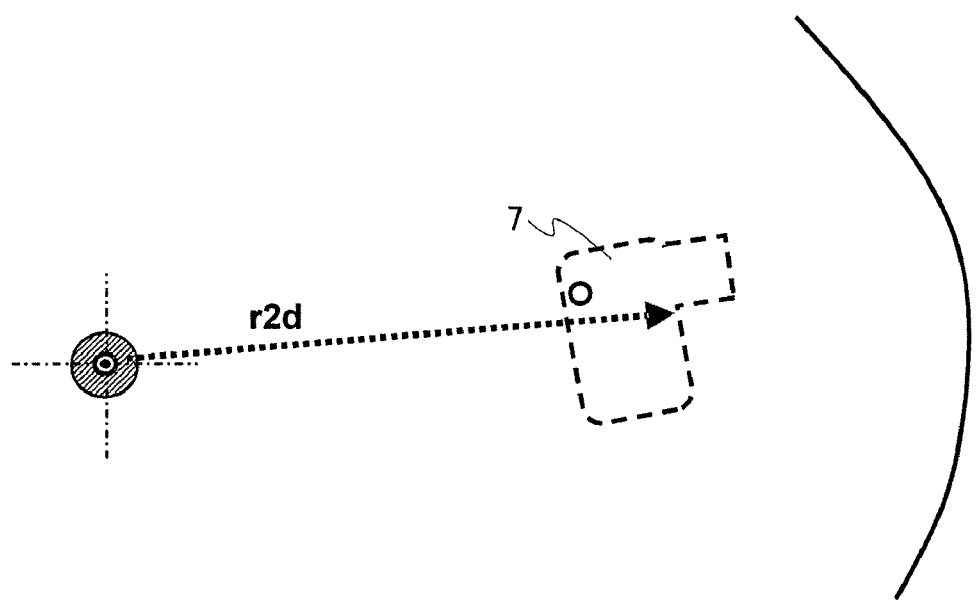
FIG. 2B is a partial top view of the substrate in FIG. 2A.

Referring to FIGS. 2A and 2B, the first example of layered structure of substrate 2 will be explained. Substrate 2 has a three-layer structure, in which upper plate material 41, chamber plate material 43 and lower plate material 44 are stacked.

Injection inlet 12 (air opening) which is provided in upper plate material 41, penetrates the upper plate material in the thickness direction. A slot hole penetrates chamber plate material 43 in the thickness direction, the slot hole which has a shape to match supply destination chamber 7. Lower plate material 44 forms the bottom surface of supply destination chamber 7, and grooves or holes are not provided in lower plate material 44. FIG. 2B is a top view of the substrate in FIG. 2A.

The three-layered substrate 2 shown in FIG. 2A can be formed by stacking the plate materials, so that the substrate is excellent in terms of the productivity. The thickness of chamber plate material 43 sets depth 25 of supply destination chamber 7. Further, lower plate material 44, which is made to be the bottom surface of supply destination chamber 7, is a separate member from other plate materials, and therefore the lower plate material is allowed to carry reaction reagents easily before stacking. Reaction reagents can be carried in the bottom part of supply destination chamber 7 for the purpose of reacting with liquid.

To stack the plate materials, arbitrary methods known by one skilled in the art may be employed. For example, adhesive materials or sheets may be interposed between the plate materials, and other adhesion methods such as ultrasonic adhesion, thermocompression and lamination may be employed. The flow paths and chambers may be formed by various methods known by one skilled in the art. For example, a photolithography represented by a semiconductor micromaching technology, an injection molding represented by plastic molding, a cutting, and a transcription for making duplicates from a master, may be employed. Potolithography is preferable for use.

The liquid transfer method using substrate 2 in Embodiment 1 will be explained using the flow chart in FIG. 3 and FIGS. 4A to 4C. The method of liquid transfer includes: (1) step A of retaining droplet 10 on retaining area 16 in first inner face 8; and (2) step B of rotating substrate 2 about rotating axis 3 at the third rotating speed rpm$_3$. In step A, the method of providing liquid 10 in supply destination chamber 6 is arbitrary.

Figure 4A:
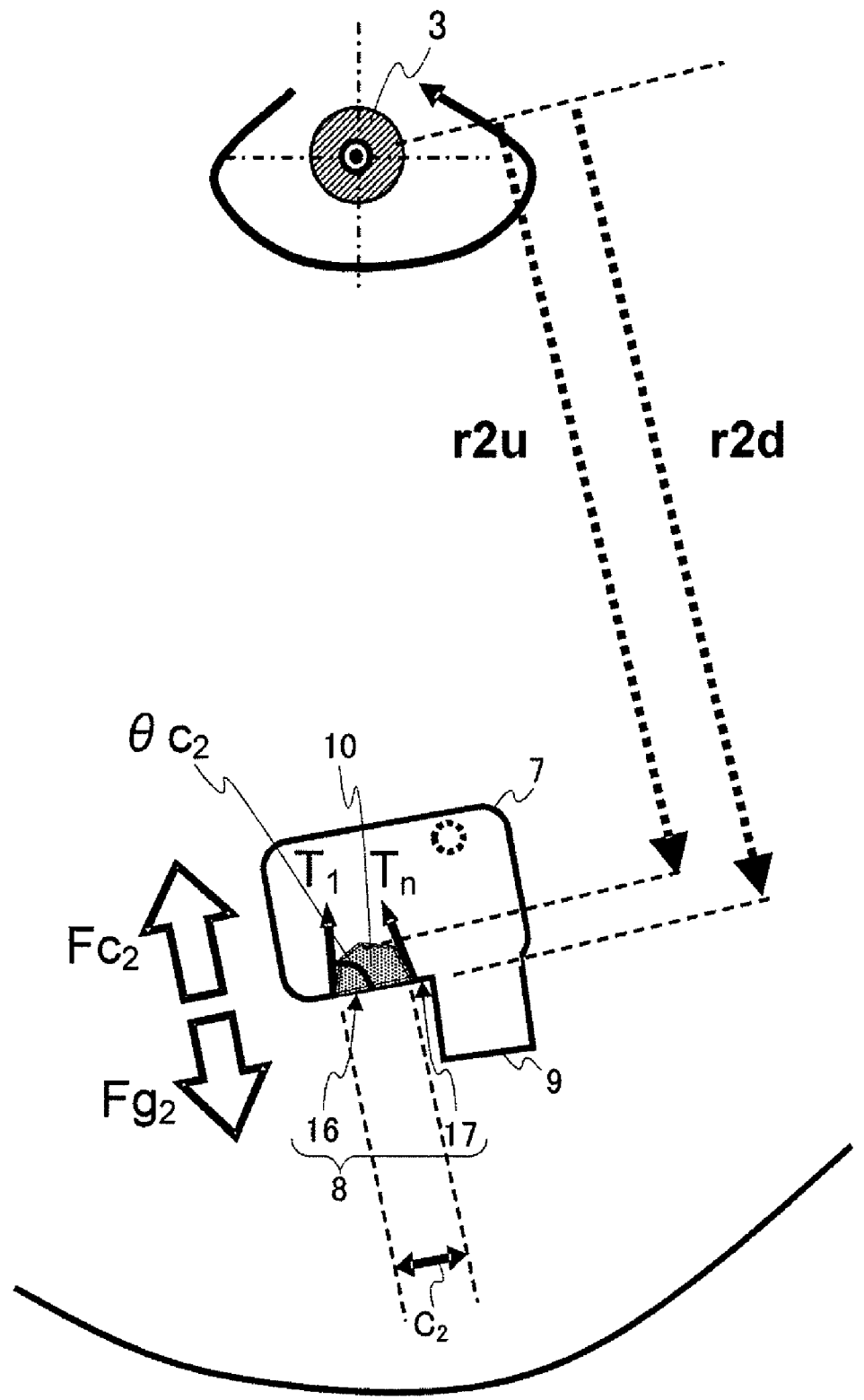
FIG. 4A is a schematic cross-sectional view to explain the force applied to liquid droplet upon rotating the substrate according to Embodiment 1, showing a state where the droplet is retained on a retaining area.

Referring to FIG. 4A, when retaining area 16 in first inner face 8 is hydrophobic, liquid 10 is retained in the form of droplet on retaining area 16 by its own cohesive force. As shown in FIG. 4A, droplet of liquid 10 is retained at contact angle $\theta c_2$ of the droplet with respect to retaining area 16 in first inner face 8. Over circumference $C_2$ of the droplet contacting retaining area 16, surface tensions $T_1$ to $T_n$, (surface tensions in all directions) are produced on an interface between first inner face 8 and liquid 10 to produce resultant force $Fc_2$. $Fc_2$ works along the centripetal direction, that is, the direction to rotating axis 3 from first inner face 8. Generally, the magnitude of the resultant force of surface tensions Fc and pressure Pc working on retaining area 16 by surface tensions Fc are represented in the following equations 1 and 2, where "T" is the surface tension of water, "θc" is the contact angle of liquid with respect to a wall, "c" is the contact circumference of droplet and "S" is the contact area of droplet.

$$Fc = T \times \cos \theta c \times c \qquad \text{(Equation 1)}$$

$$Pc = T \times \cos \theta c \times c / S \qquad \text{(Equation 2)}$$

The resultant force of surface tensions $Fc_2$, with which liquid 10 in supply destination chamber 7 is retained on retaining area 16 in first inner face 8, is produced by non-wetting effect based on the hydrophobicity of retaining area 16. Further, to retain liquid 10 on first inner face 8 by the resultant force of surface tensions Fc$_2$, the area of first inner face 8 needs to be larger than the cross-sectional area where droplet contacts. In Embodiment 1, the width of first inner face 8 (including the retaining area and the expansion area) in a plan view is set between approximately 1.5 and 18 mm. To be more specific, the width assumes between 1.75 and 7.5 mm. The depth of first inner face 8 is approximately between 0.2 and 1 mm.

FIG. 4A shows liquid 10 when substrate 2 rotates at the first rotation speed rpm$_1$, which is slower than the third rotation speed rpm$_3$. As shown in FIG. 4A, upon rotating substrate 2, centrifugal force Fg$_2$ along radial direction "r" works on liquid 10 retained on retaining area 16 by the resultant force Fc$_2$. In FIG. 4A, "r2$d$" represents the rotation radius of the imaginary bottom surface of the liquid on first inner face 8, and "r2$u$" represents the minimal rotation radius of imaginary top surface of the liquid on the first inner face 8. As shown in equation 3, the magnitude of centrifugal force Fg is proportional to the volume of liquid on which centrifugal force works; proportional to the rotation radius, or the distance from the rotating axis to first inner face 8; and proportional to the square of the rotation speed. Here, the actual magnitude of Fg shown in equation 3 can be estimated by the volume of liquid which is calculated by integrating micro-volume elements dV from minimum, rotation radius r2$u$ to maximum rotation radius r2$d$. In equation 3, symbol "p" is the density of liquid, symbol "V" is the volume of liquid on which centrifugal force Fg works, symbol "r" is the rotation radius and symbol "ω" is the angular velocity.

$$Fg' = \rho V \times r \times \omega^2 \quad \text{(Equation 3)}$$

Equation 4 holds the following relationship between the rotation speed rpm and the angular velocity ω.

$$rpm = \frac{\omega}{2\pi} \times 60 \quad \text{(Equation 4)}$$

When centrifugal pressure Pg$_2$ that works on retaining area 16 produced by centrifugal force Fg$_2$ is canceled out with the resultant force of surface tensions Pc$_2$ working on retaining area 16 by resultant force Fc$_2$, the droplet stays on first inner face 8 while the substrate rotates. As the rotation speed increases, the shape of droplet of liquid 10 becomes flat and the droplet spread to the expansion area.

Figure 4B:
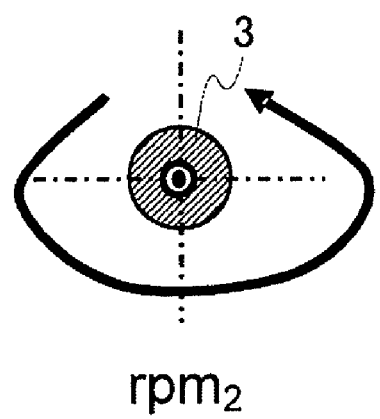
FIG. 4B is a schematic cross-sectional view to explain force applied to liquid droplet upon rotating the substrate according to Embodiment 1, showing a state where the droplet spreads by centrifugal force.
Figure 4B:
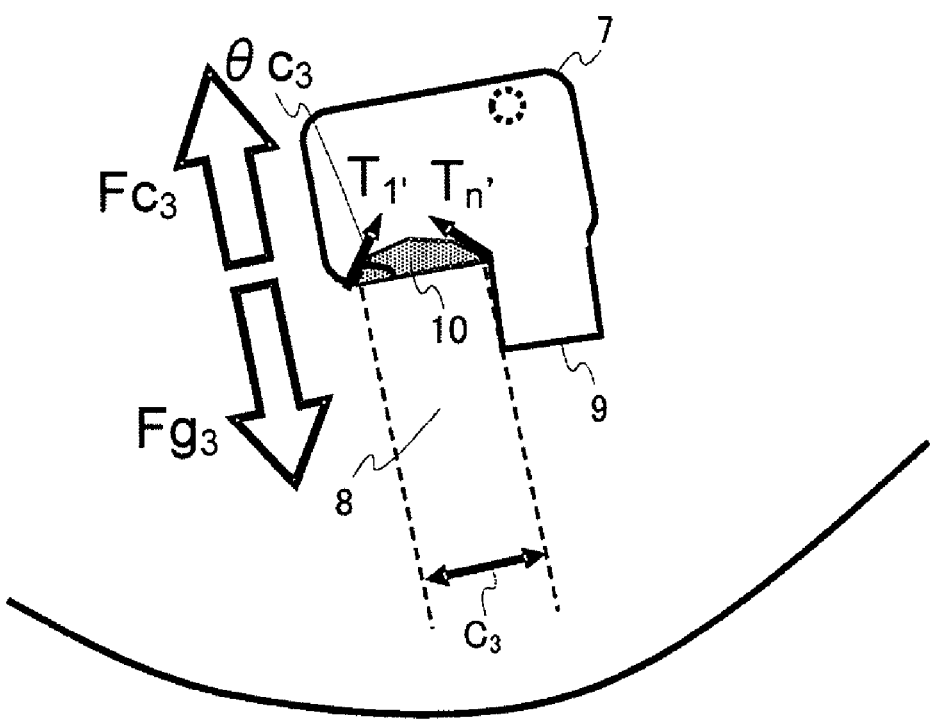

FIG. 4B shows the shape of liquid 10 while substrate 2 is rotated at the second rotation speed rpm$_2$. The second rotation speed rpm$_2$ is faster than the first rotation speed rpm$_1$ and slower than the third rotation speed rpm$_3$. As shown in FIG. 4B, by an increase of the rotation speed, centrifugal force changes from Fg$_2$ to greater Fg$_3$. To balance with Fg$_3$, the resultant force of surface tensions changes from Fc$_2$ to greater Fc$_3$. And the contact angle of droplet of liquid 10 in a plan view changes θc$_2$ to smaller θc$_3$.

By making smaller the contact angle of droplet of liquid 10, the contact circumference of droplet increases. The increased circumference is shown as "C$_3$" in FIG. 4B. In this way, droplet spreads to expansion area 17.

Figure 4C:
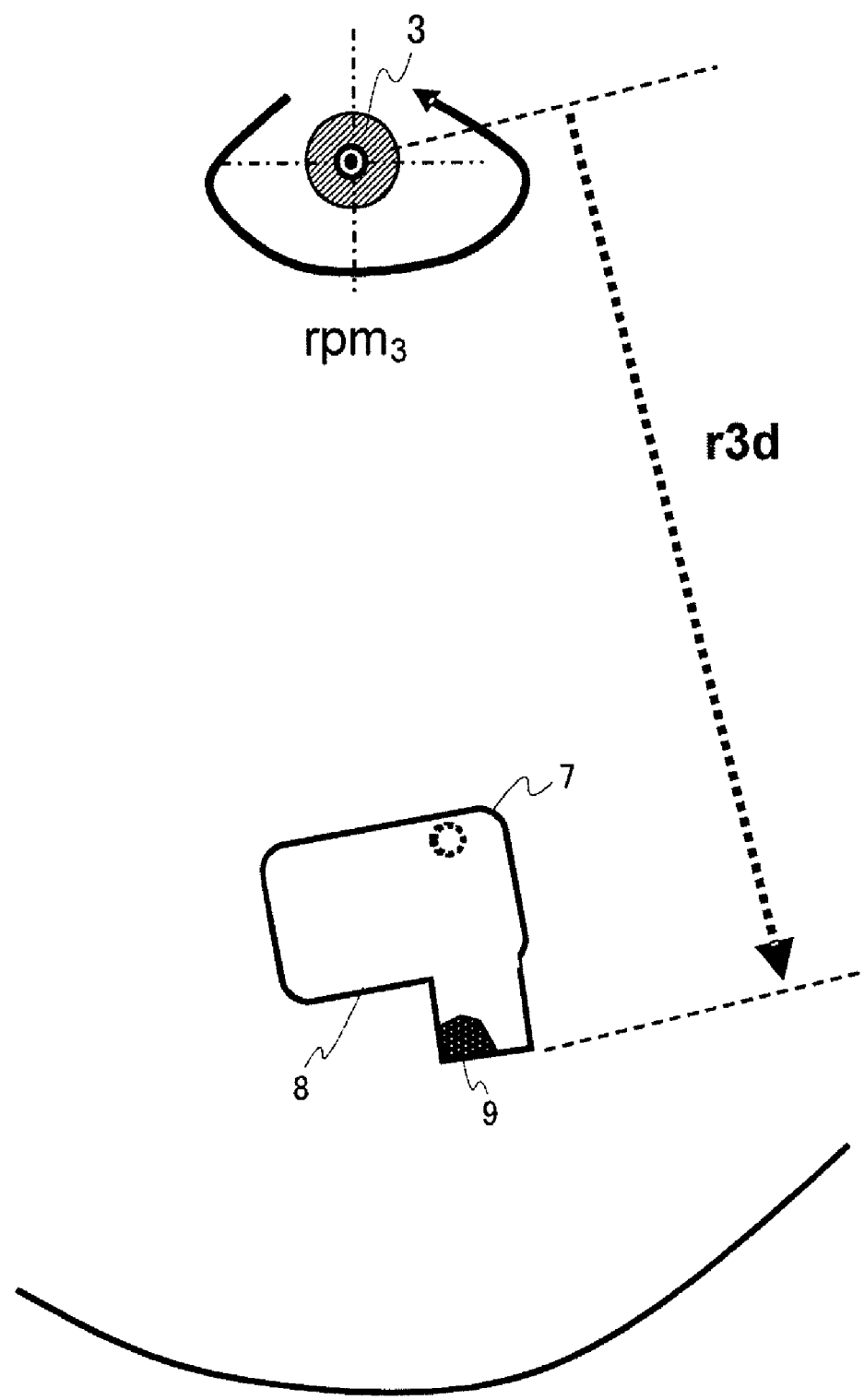
FIG. 4C is a schematic cross-sectional view to explain force applied to liquid droplet upon rotating the substrate according to Embodiment 1, showing a state where the droplet is transferred to the second inner part.

As shown in FIG. 4C, when substrate 2 is rotated at the third rotation speed rpm$_3$ faster than the second rotation speed rpm$_2$, the droplet arrive at the outermost periphery of expansion area 17. There is no area around the perimeter of expansion area 17 which receives centrifugal force along the centrifugal direction, and therefore the liquid starts to flow into second inner face 9. That is, by driving substrate 2 in rotation at the third rotation speed rpm$_3$, it is possible to transfer liquid 10 on the first inner face 8 to second inner face 9. The direction of rotation may be clockwise R1 or counterclockwise R2.

The time period and acceleration to reach the third rotation speed rpm$_3$ are set arbitrarily. Liquid 10 is retained on first inner face 8 as long as substrate 2 rotates at a slower rotation speed than the third rotation speed rpm$_3$. Then, by rotating substrate 2 at a rotation speed less than the third rotation speed rpm$_3$ in a predetermined period, it is possible to control the timing to start liquid transfer.

Liquid 10 that has flown in second inner face 9 from first inner face 8 receive centrifugal force Fg in the centrifugal direction of radial direction r and is put on the second inter face 9. When second inner face 9 is hydrophobic, liquid 10 receives surface tension Fc to be retained in the form of droplet. In FIG. 4C, "r3$d$" shows the rotation radius of second inner face 9. To be more accurate, "r3$d$" may be referred to as rotation radius of the bottom surface of liquid on second inner face 9.

Then, by providing a retaining area and an expansion area for droplet in second inner face 9 and by placing a third inner face outside the second inner face, it is possible to transfer droplet from the second inner face to a third inner face (not shown) by increasing rotation speed further.

As described above, in substrate 2 of Embodiment 1, by setting the size of expansion area adequately and rotating the substrate 2 at a third rotation speed rpm3, it is possible to transfer liquid 10 from first inner face 8 to second inner face 9, and, by repeating this, allow stepwise liquid transfer.

In this way, according to the rotation speed of substrate, liquid is transferred stepwise in a chamber having the first inner face and second inner face communicating each other. Consequently, stepwise liquid transfer is realized without a micro-flow path connecting between chambers. Since a micro-flow path does not need, produce of a substrate is easy and the production process does not involve a load.

Embodiment 2

Figure 5:
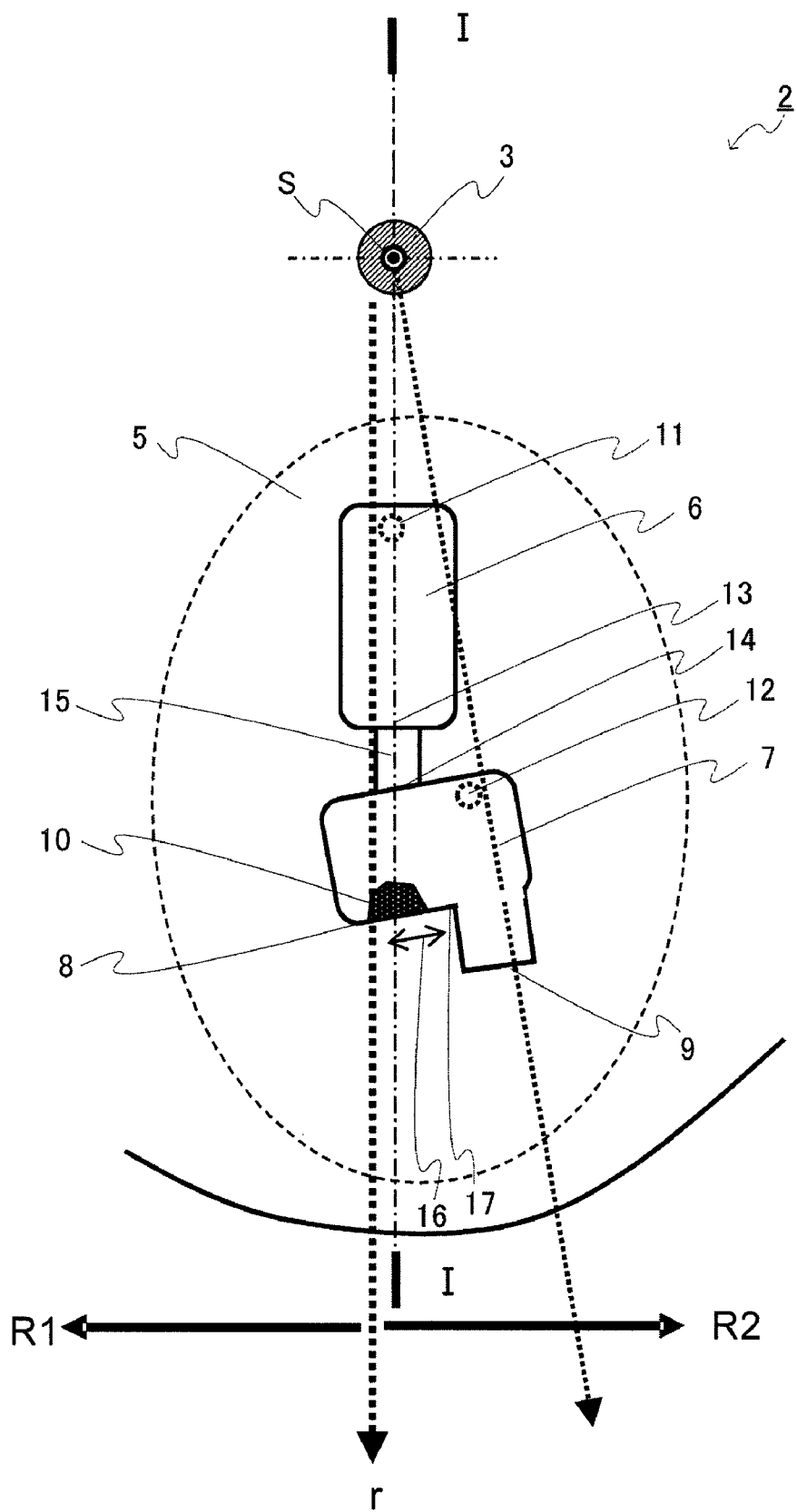
FIG. 5 is a partial cross-sectional view of the substrate according to Embodiment 2.

The structure of substrate 2 according to Embodiment 2 is shown in FIG. 5. In substrate 2 in Embodiment 2, supply source chamber 6 is provided for supply destination chamber 7 via connecting part 15. With Embodiment 1, liquid is supplied through injection inlet 12 into supply destination chamber 7. On the other hand, with Embodiment 2, droplet is provided from supply source chamber 6 to first inner face 8 in supply destination chamber 7 by rotating substrate 2.

Flow path part 5 of substrate 2 in Embodiment 2 will be explained using FIGS. 5 and 6. Referring to FIG. 5, supply source chamber 6 (the first chamber) is located closer to rotating axis 3 than supply destination chamber 7 (the second chamber) in a plan view, which communicates each other via connecting part 15.

Supply source chamber 6 is a chamber to store liquid 10 which is the target of transfer. Supply source chamber 6, which is formed inside substrate 2, is spatially closed. Referring to FIG. 5, although supply source chamber 6 has a shape of a substantially rectangular shape in a plan view. the outer shape of supply source chamber 6 is not limited to a substantially rectangular shape, and may be set arbitrarily including a pillar shape.

Injection inlet 11, which is formed on supply destination chamber 6, is a circular cross-section communicating inside of supply source chamber 6 with the outside of substrate 2. Certainly, the shape of injection inlet 11 is arbitrary. Injection inlet 11 is used to inject liquid 10 into supply source chamber 6.

Injection inlet 11, which is provided in supply source chamber 6, is located in a position closer to rotating axis 3 than first connecting end part 13. To be more specific, injection inlet 11 is located in the centripetal side of supply source chamber 6 as shown in FIG. 5. Further, the area of injection inlet 11 in a plan view is substantially smaller than the area of supply source chamber 6 in a plan view. By setting the position and area of injection inlet 11, liquid 10 flows into connecting part 15 by centrifugal force when substrate 2 is rotated, without leaking through or scattering through injection inlet 11. Therefore, in cases where the position and area of injection inlet 11 are set in this way, it is possible to inject liquid 10 in supply source chamber 6 and rotate substrate 2 while injection inlet 11 is open.

In contraries, in cases where injection inlet 11 provided in supply source chamber 6 is located more distant position from rotating axis 3 than first connecting end part 13 and where the area of injection inlet 11 is relatively large with respect to the area of supply source chamber 6, substrate 2 is preferably rotated after injection inlet 11 is sealed. The reason is, due to rotation of substrate 2, to prevent liquid 10 in supply source chamber 6 from leaking or scattering through injection inlet 11.

The dimensions and volume of supply source chamber 6 need to be determined according to the amount of sample liquid (i.e. liquid 10), and the volume of supply source chamber 6 is preferably between 0.1 and 100 μL.

Air opening 12 of supply destination chamber 7 is not used to inject liquid, which is different from as shown in Embodiment 1. Air opening 12 has functions of letting air inside supply destination chamber 7 out to the outside of substrate 2 when liquid 10 is injected in supply destination chamber 7. The number of air opening 12 may be one, or a plurality of air openings may be placed for the same use.

Supply source chamber 6 and supply destination chamber 7 is communicated in fluid each other through connecting part 15. Connecting part 15 is a flow path for transferring liquid 10 in supply source chamber 6 to supply destination chamber 7. Connecting part 15, which is formed inside substrate 2, is spatially closed. Further, both ends of connecting part 15, that is, input end part 13 (the first connecting end part) and output end part 14 (the second connecting end part), are connected to supply source chamber 6 and supply destination chamber 7, respectively.

Connecting part 15 extends from first connecting end part 13 to second connecting end part 14 along centrifugal direction "r." The cross-sectional area of first connecting end part 13 is smaller than the cross-sectional area of supply source chamber 6. The cross-sectional area of connecting part 15 is preferably the same or smaller than the both of areas of supply source chamber 6 and supply destination chamber 7.

Figure 6A:
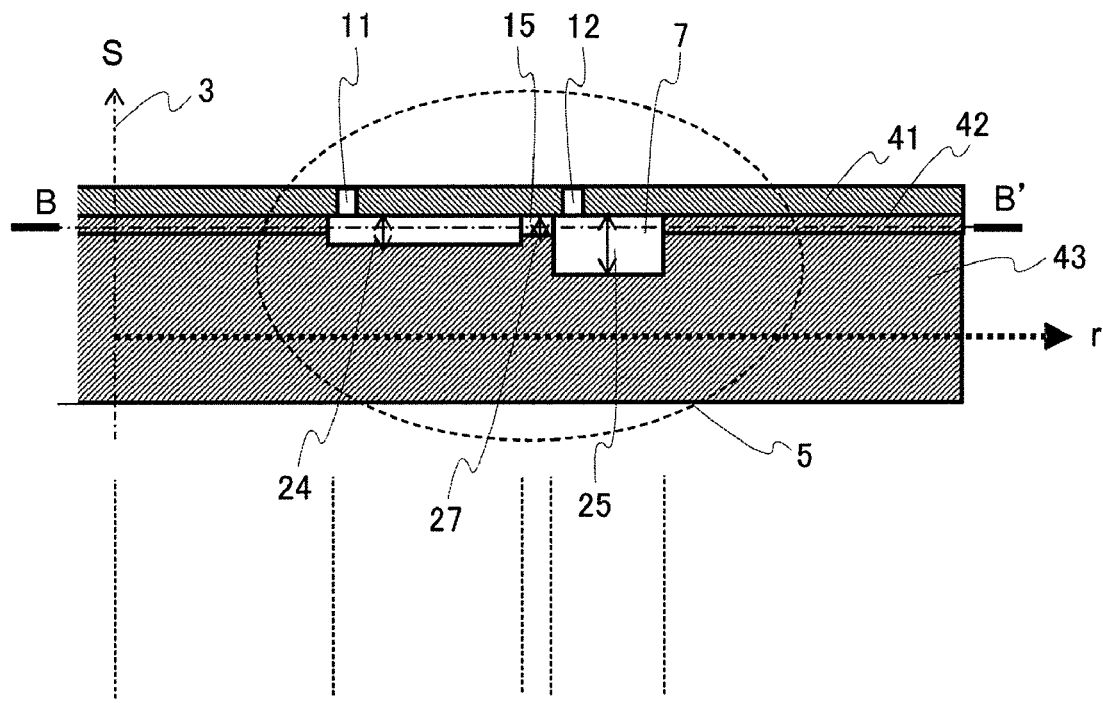
FIG. 6A is a partial cross-sectional view along I-I line in FIG. 5.
Figure 6B:
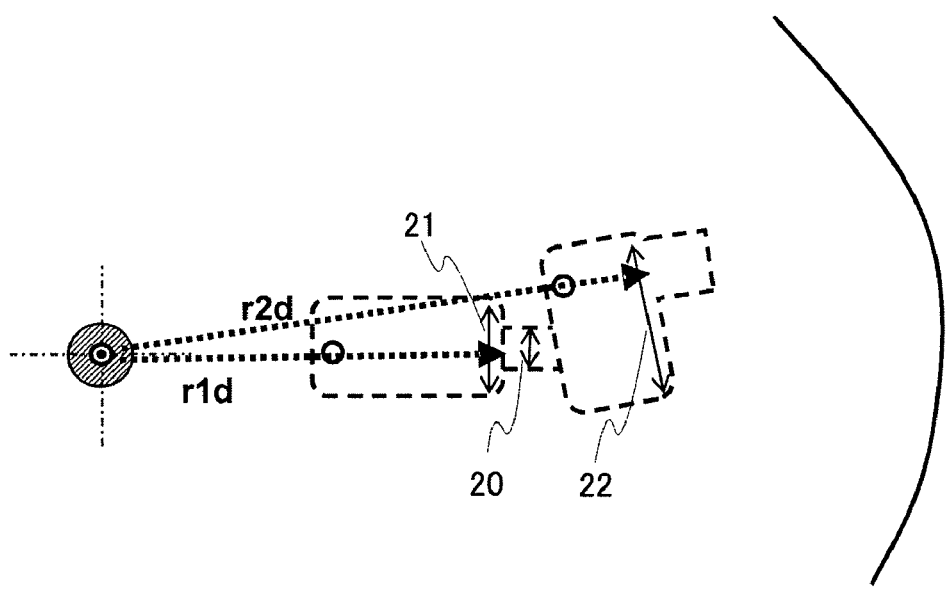
FIG. 6B is a partial top view of the substrate in FIG. 6A.
Figure 7:
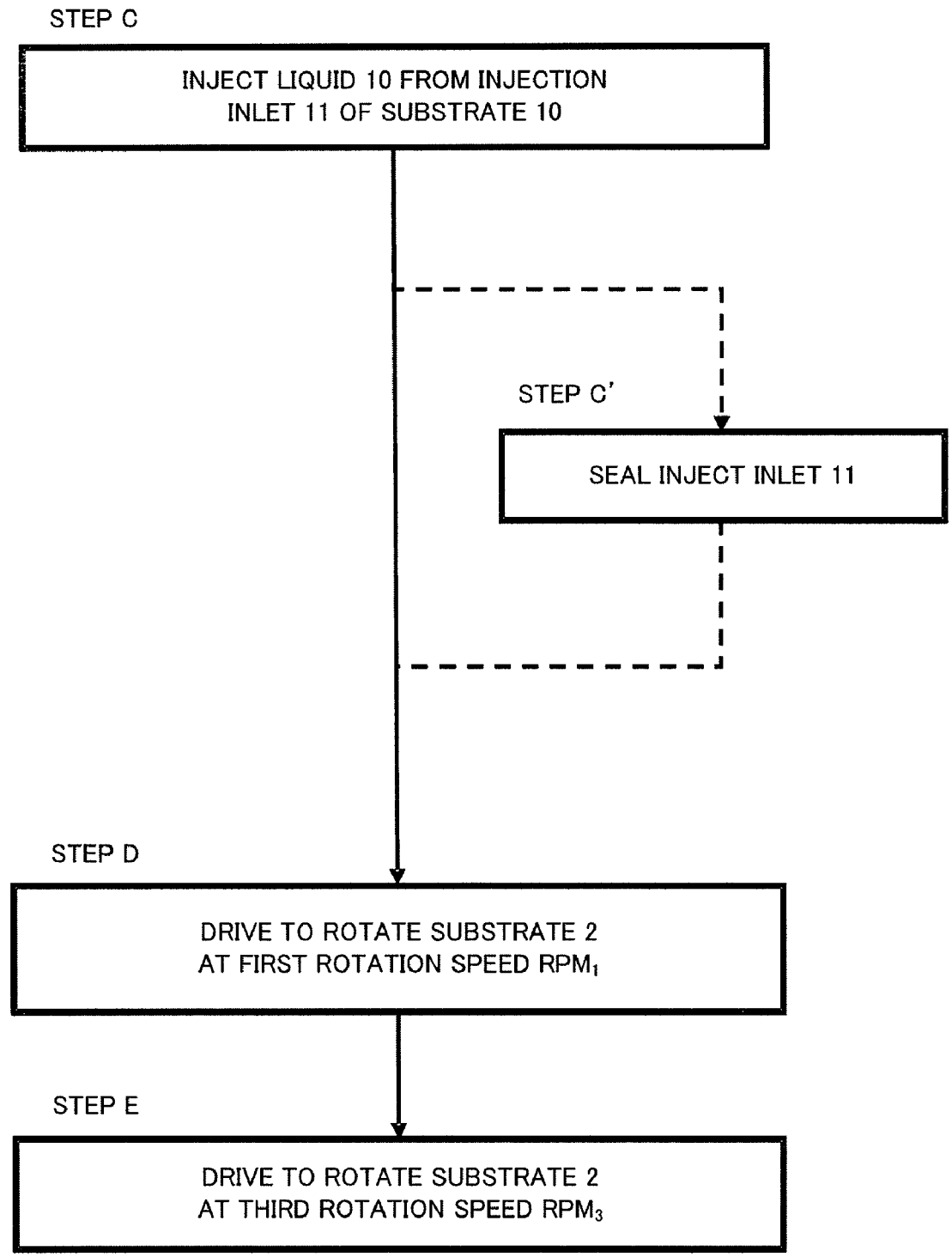
FIG. 7 is a flow chart showing the method of transferring liquid using the substrate according to Embodiment 2.

As shown in FIG. 6A, depth 27 of connecting part 15 is preferably shallower than depth 24 of supply source chamber 6 and depth 25 of supply destination chamber 7. As shown in FIG. 6B, width 20 of connecting part 15 is preferably narrower than width 21 of supply source chamber 6 and width 22 of supply destination chamber 7. Specific range values of these are as described above. The connecting part may be made relatively larger than that of so-called "micro-flow path."

First connecting end part 13 on the edge of connecting part 15 that connects supply destination chamber 6 can function as a valve for liquid 10 in supply destination chamber 6. Connecting part 15 extends from first connecting end part 13 in the centrifugal direction, that is, extends in the direction that is orthogonal to rotation directions of substrate 2 (clockwise direction R1 and counterclockwise direction R2) at right angles. For that reason, centrifugal force that works on liquid 10 by rotating substrate 2 allows liquid 10 in supply source chamber 6 to flow into connecting part 15.

Connecting part 15 extends from rotating axis 3 to second connecting end part 14 that connects with supply destination chamber 7. For that reason, liquid 10 that has flown in supply destination chamber 7 once is retained without flowing back. Further, the orientation of connecting part 15 is designed so that liquid 10 that flows in supply destination chamber 7 is directed to the first inner face. In FIG. 6B, "r1$d$" represents the rotation radius of supply source chamber 6, and "r2$d$" represents the rotation radius of first inner face 8 in supply destination chamber 7.

First connecting end part 13 on the edge of connecting part 15 is hydrophobic. To make first connecting end part 13 hydrophobic, this part may be formed from a hydrophobic material, or may be subjected to hydrophobic treatment. When first connecting end part 13 is hydrophobic, the part functions as a valve as described above.

The method of transferring a liquid (liquid transfer) using substrate 2 in Embodiment 2 will be explained using a flow-chart in FIG. 7 and FIGS. 8A to 8G. The method of liquid transfer using substrate 2 of Embodiment 2 has: step D of driving substrate 2 in rotation at the first rotation speed $rpm_1$; and step E of driving substrate 2 in rotation at the third rotation speed $rpm_3$. Prior to step D, liquid 10 is injected in supply source chamber 6 through injection inlet of substrate 2 (step C). The volume of liquid 10 injected thereupon assumes to be "imaginary chamber volume 18."

Figure 8A:
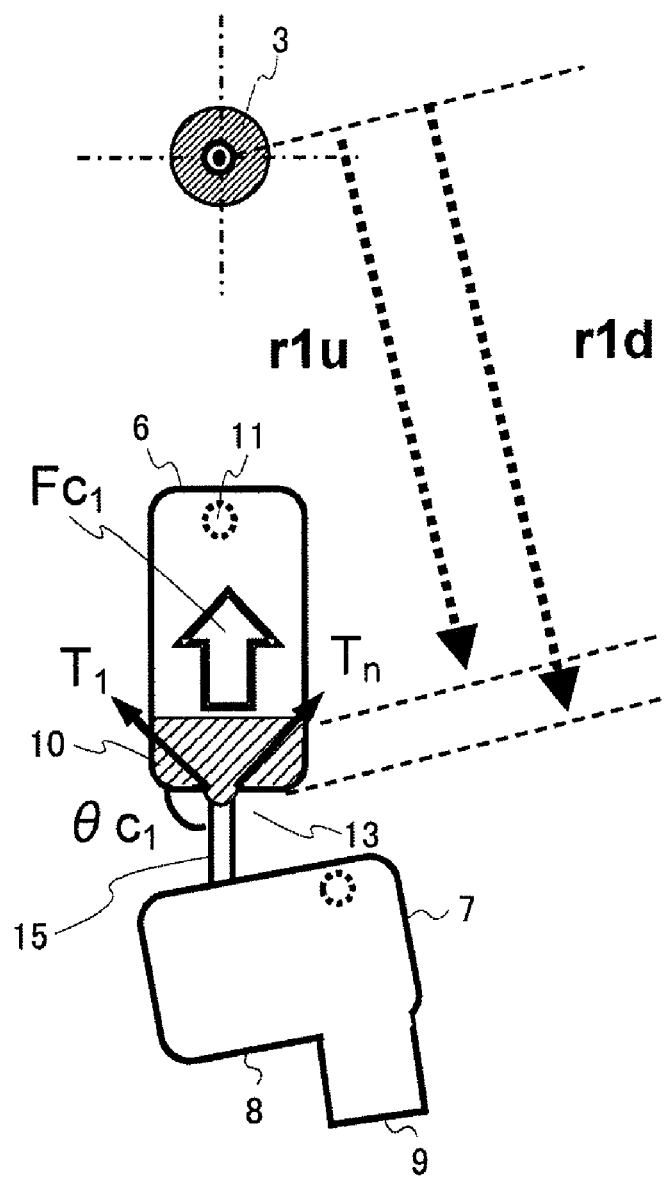
FIG. 8A is a schematic cross-sectional view to explain force applied to liquid upon rotating the substrate according to Embodiment 2, showing a state where liquid accommodated in a supply source chamber is subjected to capillary force.

Liquid 10 fed in first chamber 6 through injection inlet 11 receives the first capillary force $Fc_1$ that prevents liquid 10 from flowing in connecting part 15, in first connecting end part 13 (FIG. 8A). First connecting end part 13 on the edge of connecting part 15 is hydrophobic, and the cross-sectional area of first connecting end part 13 is smaller than the cross-sectional area of supply source chamber 6, so that liquid 10 is retained on first connecting end part 13 by the first capillary force $Fc_1$ by surface tensions, not to flow in connecting part 15.

Contact angle $\theta c_1$ of liquid 10 with respect to the wall of flow path is obtuse, so that the first capillary force $Fc_1$ to retain liquid 10 in supply source chamber 6 is produced. Specifically, surface tensions $T_1$ to $T_n$ (surface tensions in all directions) are produced on interfaces between the wall of connecting part 15 and liquid 10. And the capillary force $Fc_1$ along the centripetal direction is produced, which is the resultant force of the surface tensions. Here, the centripetal direction is inward direction of supply source chamber 6 from first connecting end part 13. Generally, the magnitude of capillary force Fc and pressure Pc by capillary force Fc on flow path end part (first connecting end part) 13 are represented by the above-described equations 1 and 2.

The capillary force $Fc_1$ that retains liquid 10 in first connecting end part 13 of supply source chamber 6, works based on non-wetting effect, and therefore works when first connecting end part 13 is hydrophobic. Further, to keep liquid 10 in first connecting end part 13 by capillary force $Fc_1$, it is important to adequately set up the cross-sectional area of connecting part 15. By setting connecting part 15 having a width between 100 and 2000 μm, and a depth that is shallower than depths of supply source chamber 6 and supply destination chamber 7, it is possible to retain liquid 10 in first connecting end part 13 by capillary force $Fc_1$.

If necessary, it is preferable that injection inlet 11 is sealed (step C' in FIG. 7) in order to prevent liquid 10 from scattering due to rotation of substrate 2. As described above, by providing injection inlet 11 in a position close to rotating axis S, scattering of liquid due to the rotation of substrate 2 is less likely. Further, by making the opening area of injection inlet 11 substantially smaller than supply source chamber 6, scattering of liquid is less likely. Meanwhile, when injection inlet 11 is open, there are cases in step C where the sufficient amount of liquid 10 cannot be injected in supply source chamber 6. Therefore, by sealing injection inlet 11, it is possible to both inject the sufficient amount of liquid 10 in supply source chamber 6 and prevent liquid 10 from scattering during rotation of substrate 2. In FIG. 8A, "r1$d$" represents the rotation radius of supply source chamber 6, and "r1$u$" represents the rotation radius of imaginary surface of liquid in supply source chamber 6.

Next, substrate 2 drives in rotation at the first rotation speed $rpm_1$ (step D). As shown in FIG. 8, when substrate 2 rotates at the first rotation speed rpm, centrifugal force $Fg_1$ along radial direction "r" works on liquid 10 retained in first connecting end part 13 by capillary force $Fc_1$. The magnitude of centrifugal force Fg is: (1) proportional to the volume of liquid on which centrifugal force works; (2) proportional to the rotation radius r1$d$ (see FIG. 8A), which gives the distance from rotating axis 3 to first connecting end part 13; and (3) proportional to the square of the rotation speed.

When the centrifugal pressure $Pg_1$ that works on first connecting end part 13 by the centrifugal force $Fg_1$ exceeds capillary pressure $Pc_1$ that works on first connecting end part 13 by the capillary force $Fc_1$, liquid 10 in first connecting end part 13 flows in connecting part 15. That is, when $Pg_1$ is smaller than $Pc_1$, liquid 10 keeps on being retained in first connecting end part 13 even when the centrifugal force $Fg_1$ works. Then, when $Pg_1$ exceeds $Pc_1$ which retains liquid 10 in first connecting end part 13, liquid 10 retained in first connecting end part 13 flows in connecting part 15.

Figure 8B:
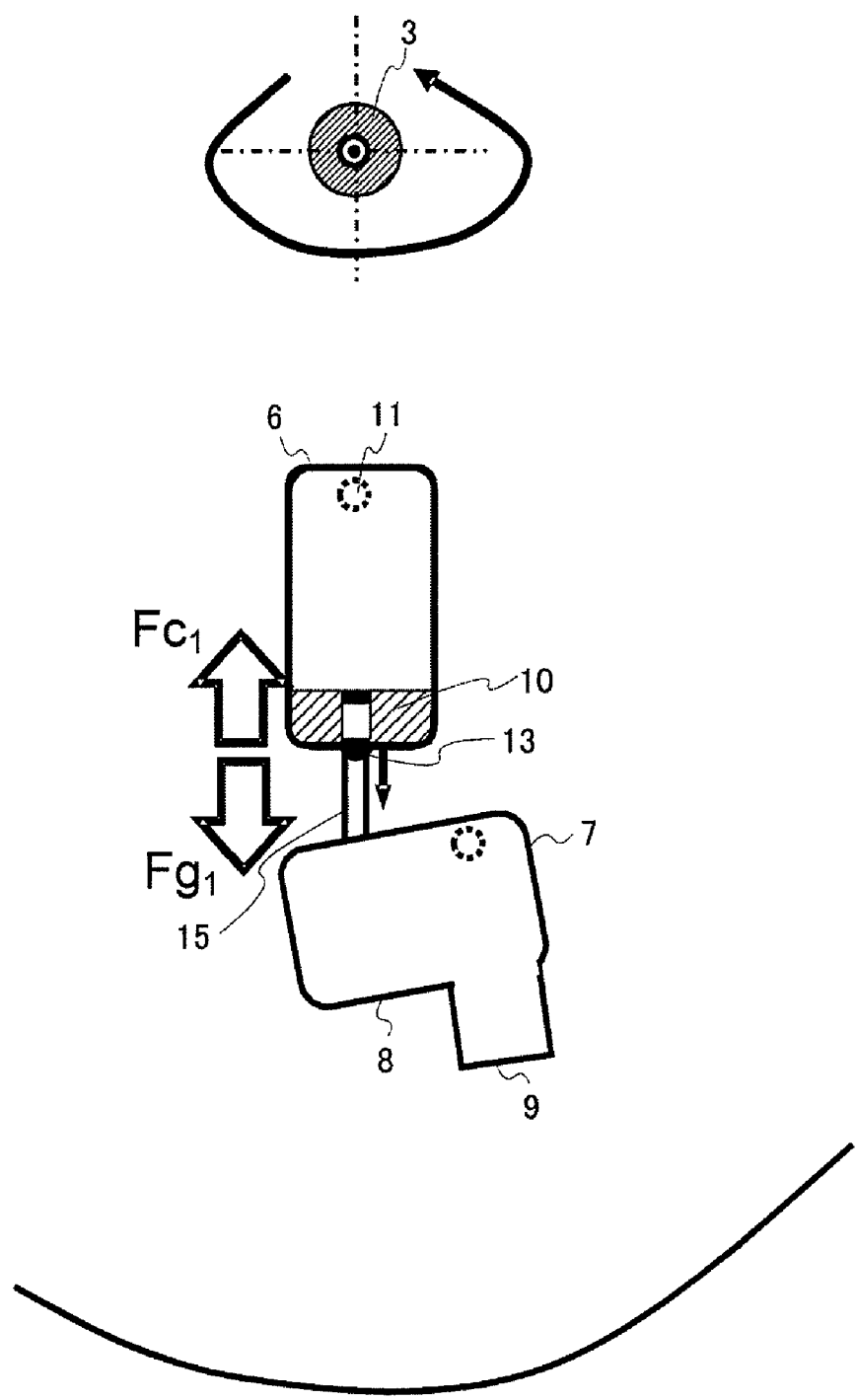
FIG. 8B is a schematic cross-sectional view to explain force applied to liquid upon rotating the substrate according to Embodiment 2, showing a state where liquid accommodated in a supply source chamber is subjected to capillary force and centrifugal force.
Figure 8C:
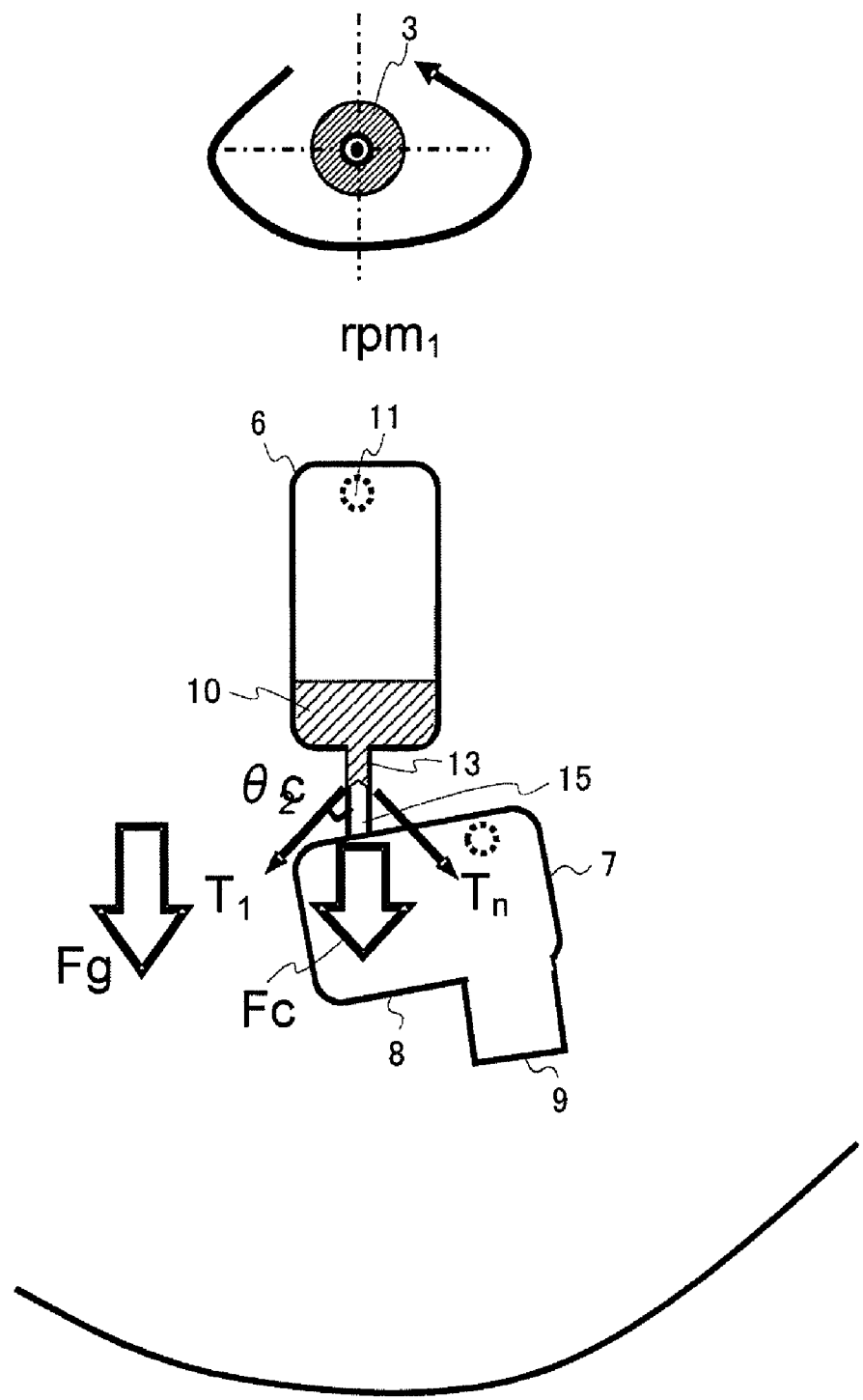
FIG. 8C is a schematic cross-sectional view to explain force applied to liquid upon rotating the substrate according to Embodiment 2, showing a state where liquid in the supply source chamber is introduced in a connecting part.
Figure 8D:
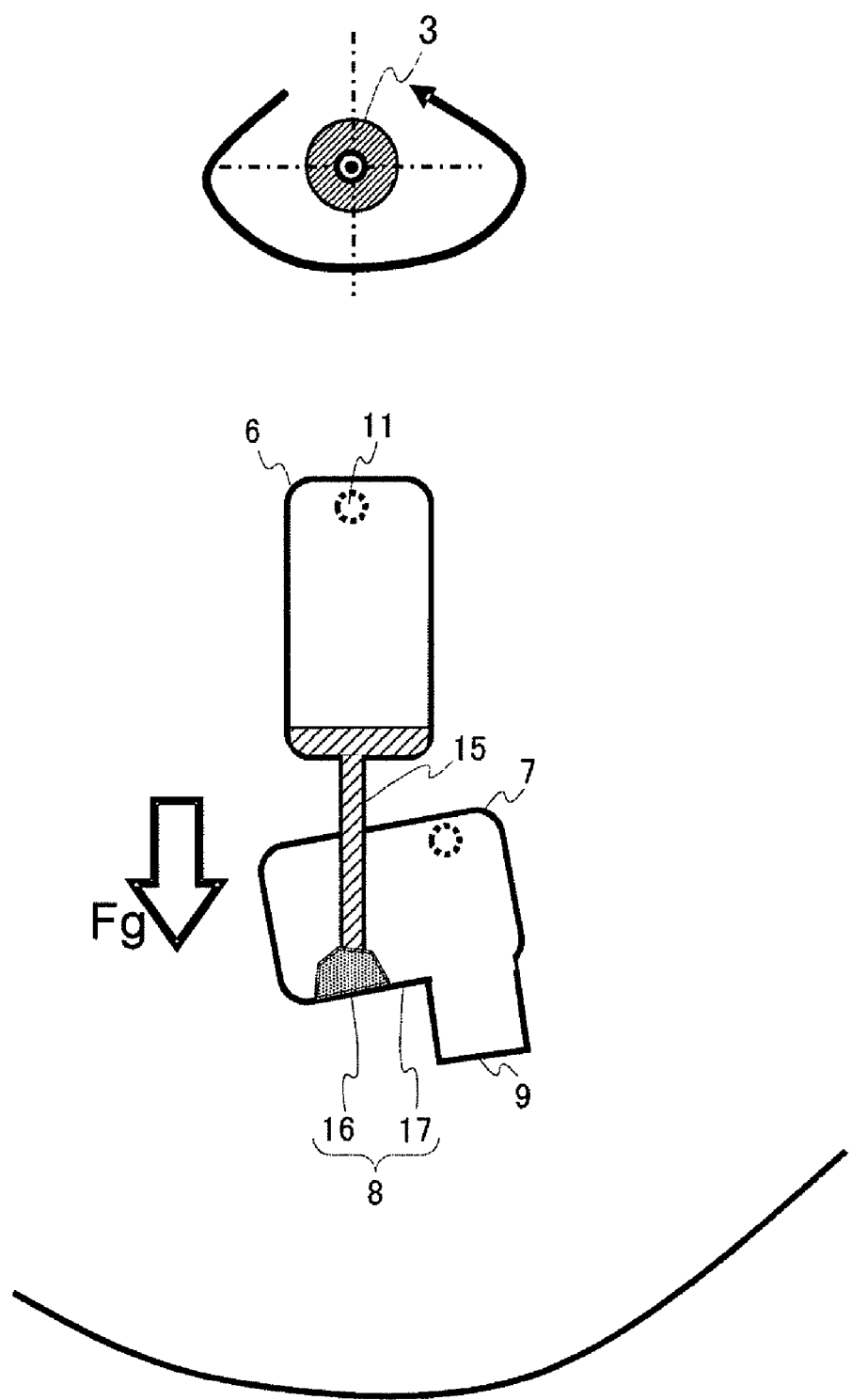
FIG. 8D is a schematic cross-sectional view to explain force applied to liquid upon rotating the substrate according to Embodiment 2, showing a state where liquid in the supply source chamber is introduced in a supply destination chamber.

The rotation speed in cases where centrifugal pressure $Pg_1$ exceeds capillary pressure $Pc_t$ assumes to be the first rotation speed $rpm_1$. By rotating substrate 2 at the first rotation speed $rpm_1$, it is possible to let liquid 10 in first chamber 6 flow in connecting part 15 (FIGS. 8B and 8C). Connecting part 15 is directed to first inner face 8, and therefore liquid 10 flowing in connecting part 15 is placed on first inner face 8. In this way, according to applying the first rotation speed $rpm_1$, liquid 10 is transferred from supply source chamber 6 to first inner face 8 in the supply destination chamber (FIG. 8D).

The timing and acceleration to reach the first rotation speed $rpm_1$ are set arbitrarily.

After liquid 10 is transferred from supply source chamber 6 to first inner face 8 (FIGS. 8E to 8G), liquid 10 may be transferred from first inner face 8 to second inner face 9 at the third rotation speed $rpm_3$, similar to Embodiment 1.

Figure 8E:
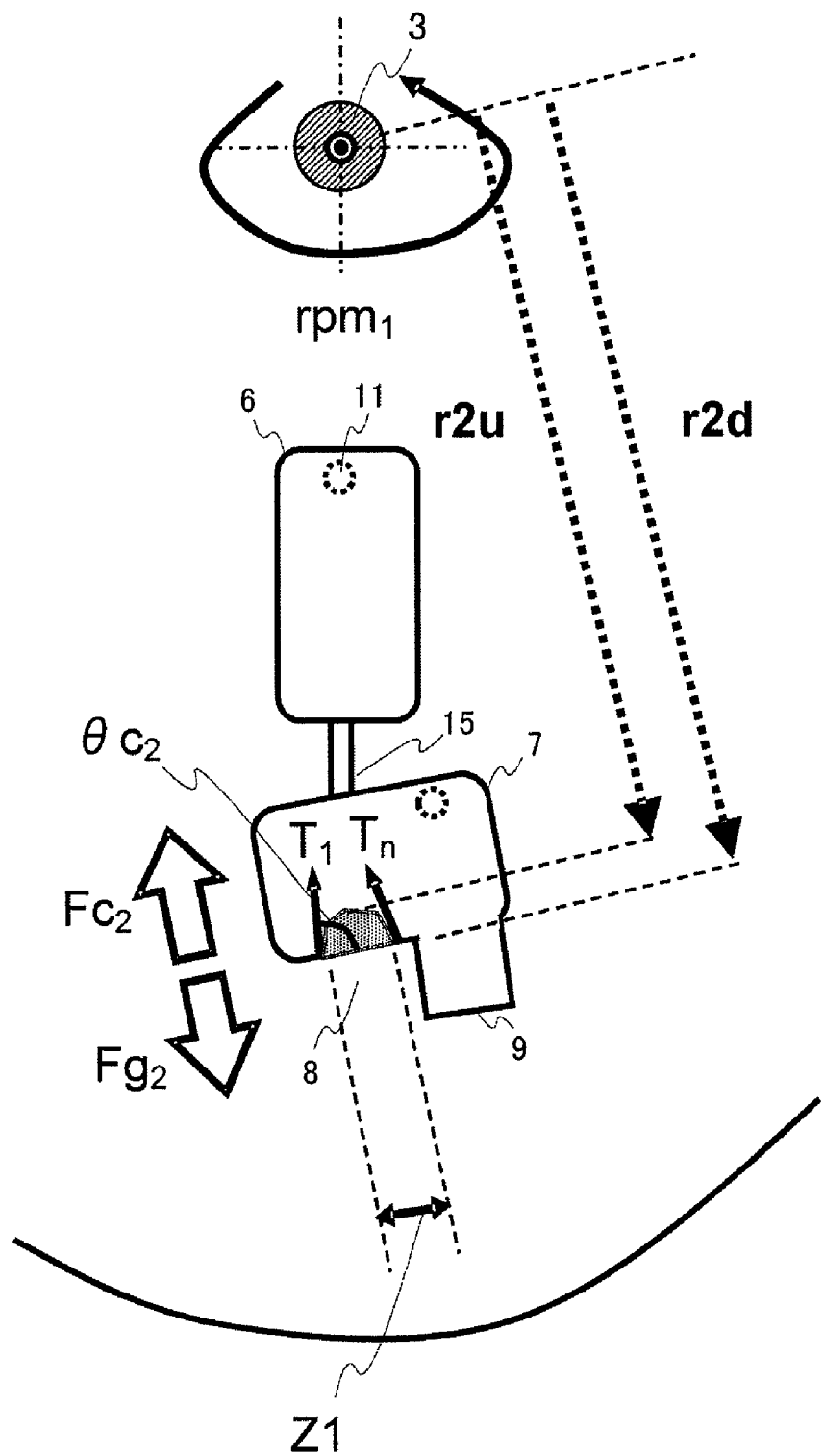
FIG. 8E is a schematic cross-sectional view to explain force applied to liquid upon rotating the substrate according to Embodiment 2, showing a state where droplet is retained on the retaining area in the supply destination chamber.
Figure 8F:
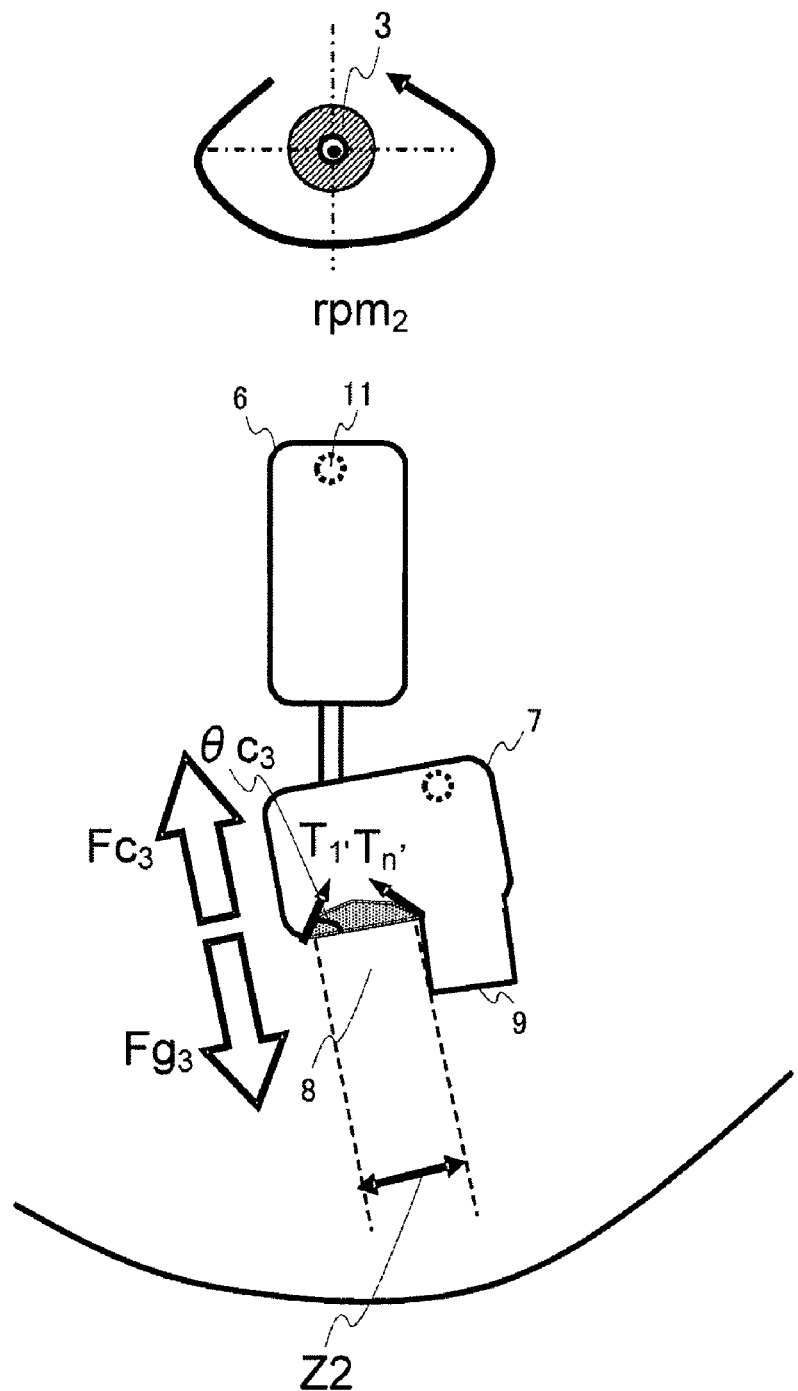
FIG. 8F is a schematic cross-sectional view to explain force applied to liquid upon rotating the substrate according to Embodiment 2, showing a state where the droplet spreads by centrifugal force.
Figure 8G:
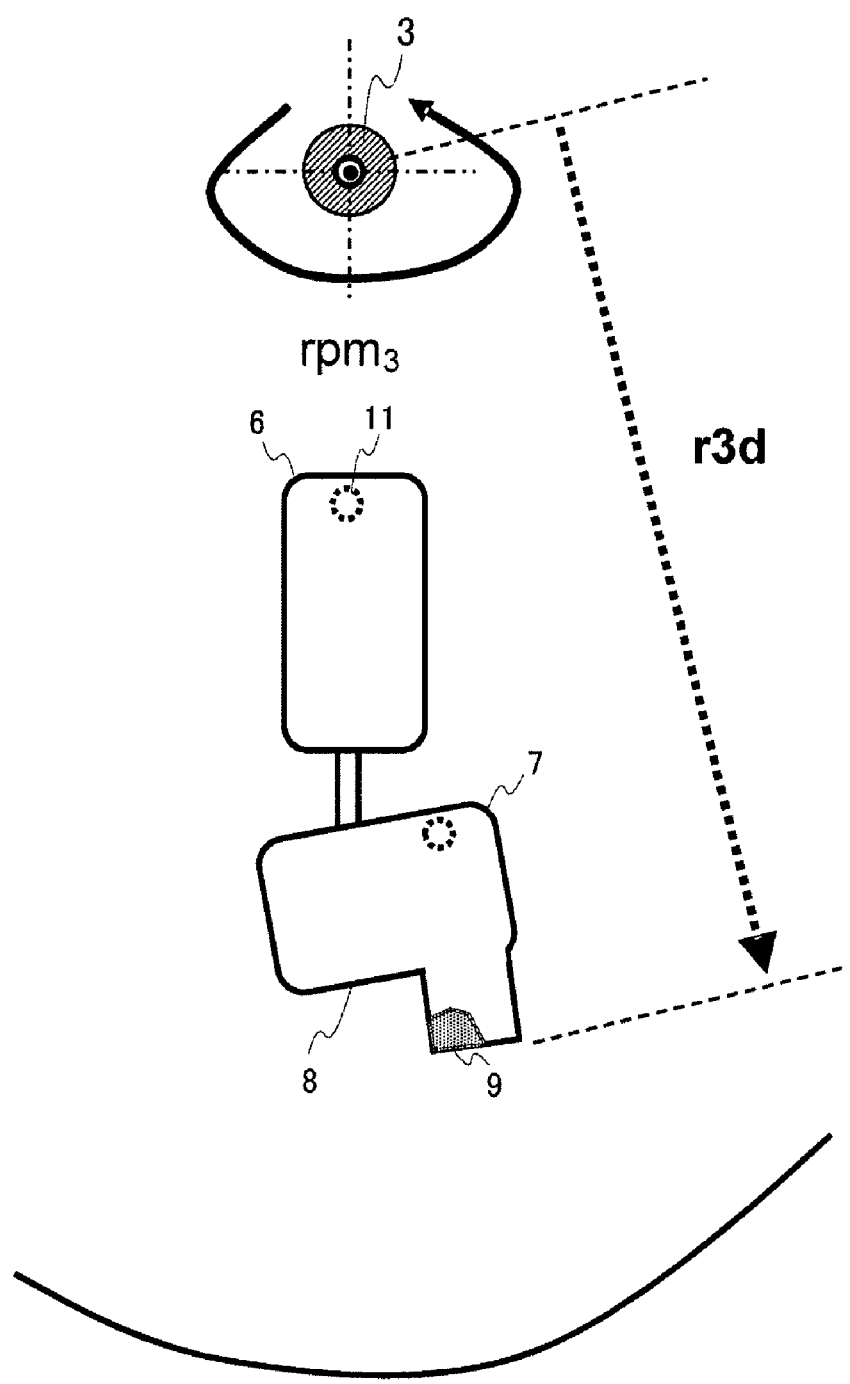
FIG. 8G is a schematic cross-sectional view to explain force applied to liquid upon rotating the substrate according to Embodiment 2, showing a state where the droplet is transferred to the second inner part.

As described above, by rotating substrate 2 of Embodiment 2 in rotation at the first rotation speed $rpm_1$, it is possible to transfer liquid 10 from first chamber 6 to second chamber 7, and, by rotating substrate 2 of Embodiment 2 at the third rotation speed $rpm_3$, it is possible to transfer liquid 10 from first inner face 8 to second inner face 9. In this way, stepwise liquid transfer is realized. In FIG. 8E, "r2$d$" represents the rotation radius of first inner face 8, and "r2$u$" represents the rotation radius of imaginary surface of liquid on the first inner face 8. In FIG. 8G, "r3$d$" represents the rotation radius of second inner face 9.

A Second Example of Layered Structure of Substrate 2

Referring to FIG. 6, a second example of the layered structure of substrate 2 will be explained. Substrate 2 shown in FIG. 6 has a three-layer structure, which includes upper plate material 41 having air hole 12; connecting member 42 in which the connecting part is provided; and chamber plate material 43 in which supply source chamber 6 and supply destination chamber 7 are provided. A slot hole is provided in chamber plate material 43. The slot hole has a shape corresponding to supply source chamber 6 and supply destination chamber 7, and does not penetrate in the thickness direction. This chamber plate material 43 can be produced by cutting. Further, by using a cut member as a metal mold, the chamber plate may be molded in one piece by resin molding. Connecting member 42, in which slot holes are provided corresponding to the connecting part, supply source chamber 6 and supply destination chamber 7 respectively, and penetrate in the thickness direction. This connecting member 42 is formed by punching a resin film and a sheet-metal. These processes are excellent in mass production and preferable in terms of cost.

Embodiment 3

Figure 9A:
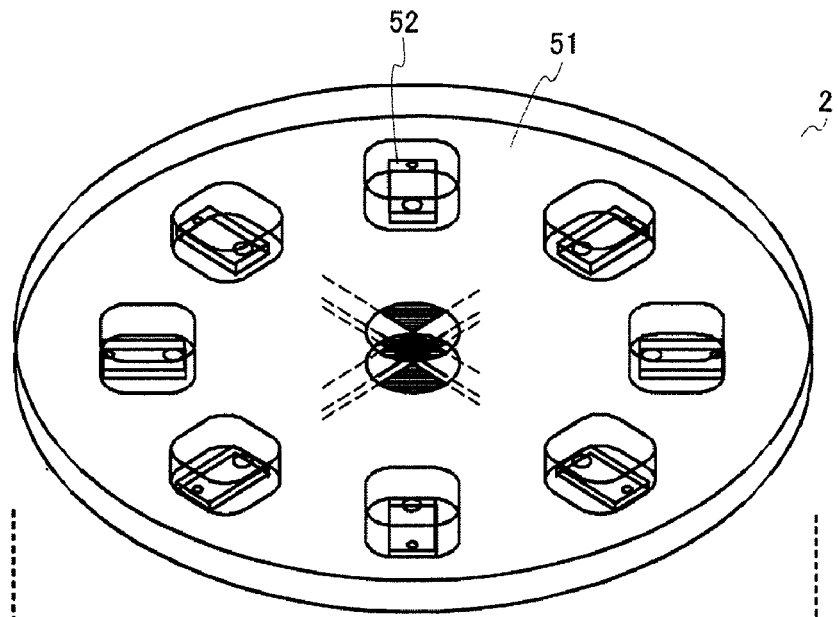
FIG. 9 is a schematic diagram showing the substrate according to Embodiment 3.
Figure 9B:
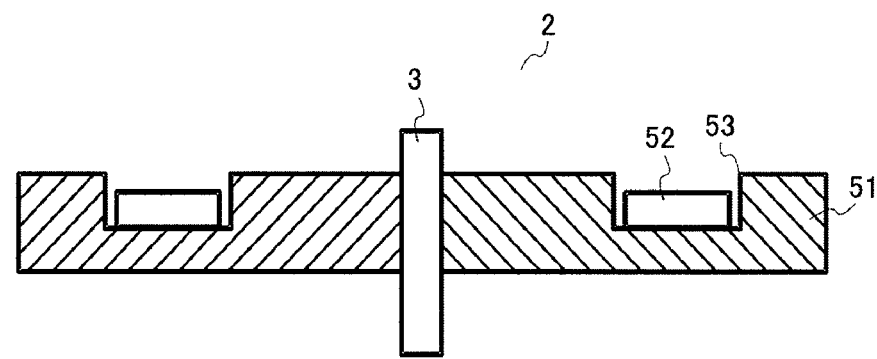

Substrate 2 in Embodiment 3 shown in FIGS. 9A and 9B has: substrate body 51; and chips 52, which are removable from substrate body 51. A flow path part is formed in each chip 52, and is not formed in substrate body 51. A plurality of accommodating holes 53 are formed on the top face side of substrate body 51, a plurality of chips 52 is accommodated in each of accommodating holes 53. Accommodating holes 53 are arranged radially. Concave parts are formed on the outer wall surfaces of accommodating holes 53.

Chips 52 accommodated in accommodating holes 53, are held in accommodating holes 53. By centrifugal force due to rotation of substrate 2, chips 52 are urged toward the outer periphery side, and therefore it is preferable that chips 52 are definitely held in rotating substrate body 51 so that chips 52 are not got out from accommodating holes 53.

Other configurations and effects in Embodiment 3 are the same as in Embodiment 1.

Liquid Transfer Apparatus

Figure 10:
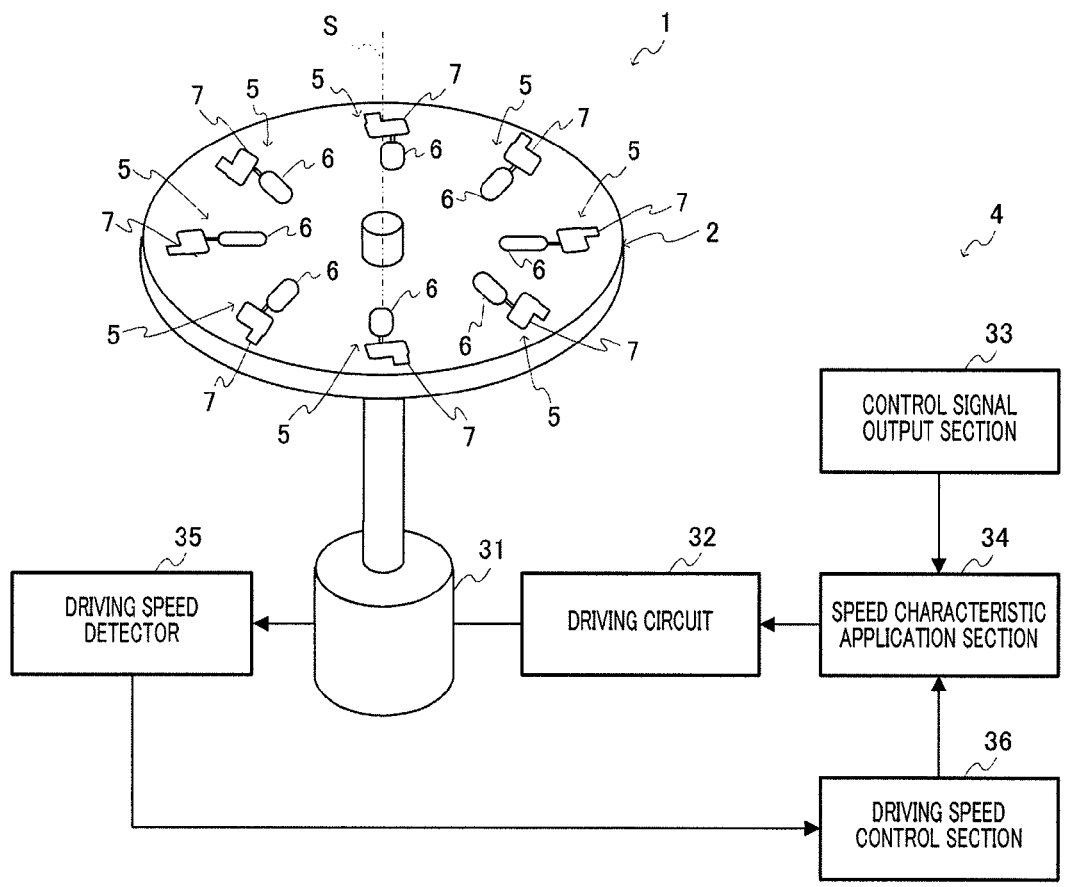
FIG. 10 is a schematic diagram showing the liquid transfer apparatus of the present invention.

The liquid transfer apparatus of the present invention will be explained with reference to FIG. 10. As shown in FIG. 10, apparatus 1 has: substrate 2; rotating shaft 3 where substrate 2 is fixed; and rotation drive part 4 that drives rotating axis 3 in rotation. Axis S of rotating shaft 3 (the center axis of rotation) extends vertically. Substrate 2 is fixed on the top side of rotating shaft 3. Substrate 2 is a circle in a plan view, and the center of substrate 2 matches axis S. Meanwhile, the bottom end of rotating shaft 3 is connected with motor 31.

A plurality of connecting parts 5 are arranged radially around rotating axis 3 on substrate 2. Outer shape of substrate 2 may be set arbitrary with dimensions that can accommodate flow path parts 5.

By providing a member of a central axis that works as the center of rotation, the substrate itself can be rotated without preparing a mechanism to mount on the rotation drive part, so that the liquid transfer apparatus becomes more convenient. Further, a substrate having a central shaft is effective in lowering the cost to process one sample from the aspect of the manufacturing cost.

Rotation drive part 4 has: rotating axis 3; motor 31 that rotates a substrate fixed on rotating shaft 3; and driving circuit 32 of motor 31. Further, rotation drive part 4 has: control signal output section 33 that output control signals; speed characteristic application section 34 that gives desired speed characteristic to driving circuit 32 of motor 31 based on control signals received as input from control signal output section 3. Control signal output section 33 may be another computer apart from liquid transfer apparatus 1.

Rotation drive part 4 has driving speed detector 35 that detects the rotation speed of substrate 2 during rotation and has driving speed control section 36 that corrects the speed characteristic given by speed characteristic application part 34. The actual rotation speed of substrate 2 detected by driving speed control section 36 is sent to driving speed control section 36. When there is a difference between the detected actual rotation speed and the speed characteristic that should be given to motor 31 by speed characteristic application part 34, the speed characteristic given by speed characteristic application part 34 is corrected by driving speed control section 36. In this way, by driving substrate 2 while the actual rotation speed is fed back to correct speed characteristics, so that stable liquid transfer is realized and the repeatability of the amount of liquid transfer improves.

Embodiment 4

A Third Example of Layered Structure of Substrate 2

Figure 11:
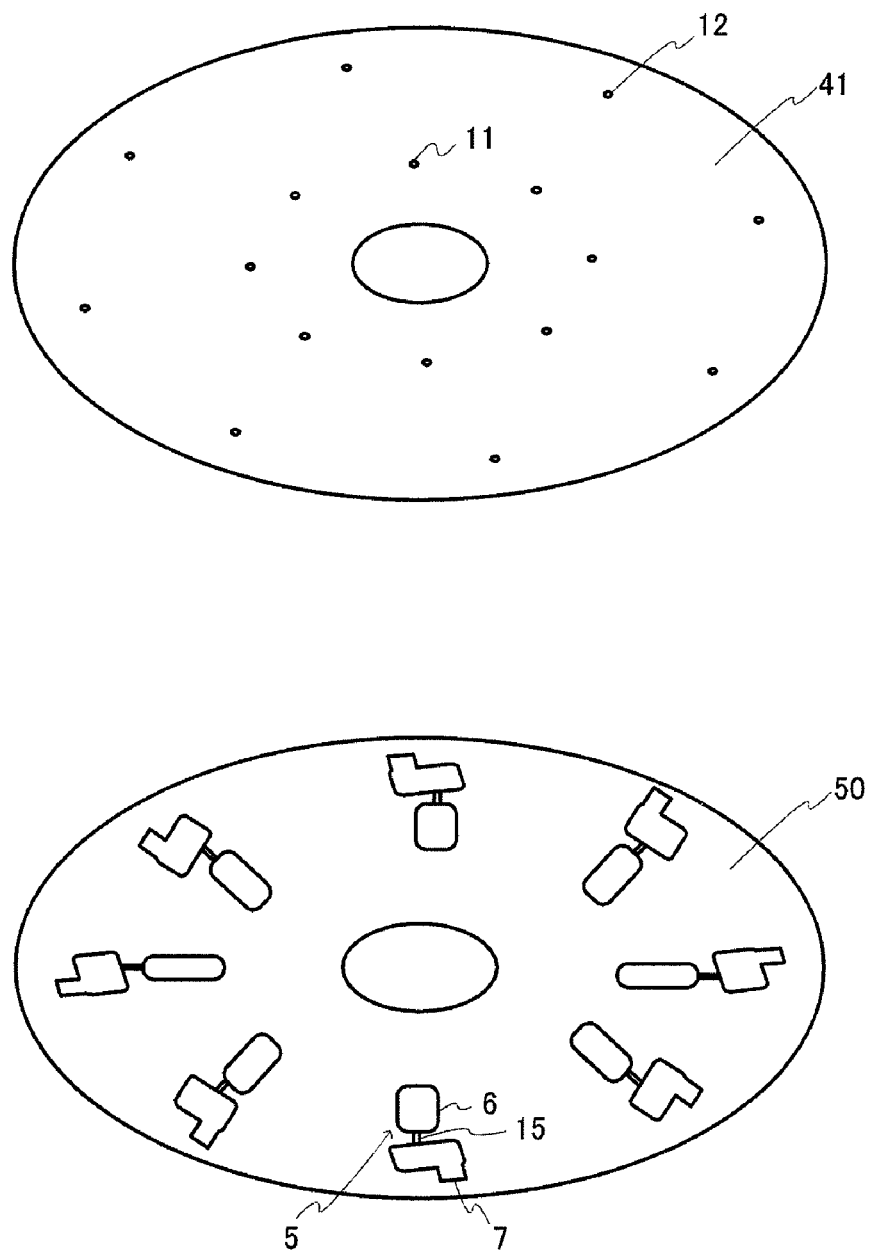
FIG. 11 is a perspective view of another configuration of the substrate.

Referring to FIG. 11, a third example of the layered structure of substrate 2 will be explained. Substrate 2 shown in FIG. 11 has two-layered structure, which includes upper plate material 41 having air hole 12; and lower plate material 50 in which supply source chamber 6, supply destination chamber 7 and connecting part 15 are provided. The two-layered structure substrate 2 shown in FIG. 11 can be produced using photolithography, for example. To be more specific, the steps include: applying photoresist to lower plate material 50 to form supply source chamber 6, supply destination chamber 7 and connecting part 15 by lithography; forming injection inlet 11 and air hole 12 in upper plate material 41; and covering the top part of flow path parts 5 in lower plate material 50 with upper plate material 41.

First, the steps of forming supply source chamber 6, supply destination chamber 7 and connecting part 15 will be explained. A thick film negative photoresist is applied to a glass substrate subjected to cleaning treatment. A photoresist suitable for the size of the flow path is selected for use. For example, KMPR1030 (Nippon Kayaku Co., Ltd) is excellent in terms of the film thickness and the aspect ratio of the hole to be formed. A spin-coating applicator such as a spincoater is used. In cases where KMPR 1030 is spin-coated by a spincoater, the spincoater is pre-rotated ten seconds at 500 rpm, followed by thirty seconds of main rotation at 1000 rpm. By changing the main rotation speed, it is possible to change the thickness of the coating film. An example shows that main rotation at 1000 rpm provides a thickness of 57 μm, and main rotation at 1070 rpm provides a thickness of 48 μm.

After that, the coating film is pre-baked for 20 minutes at 95° C., and is exposed via a mask in which flow paths and chambers are drawn. The intensity of exposure and duration of exposure may be adequately adjusted depending on the film thickness. One example of desirable intensity of exposure is approximately 1700 mJ/cm². Next, PEB (Post Exposure Bake) is performed for 6 minutes at 95° C., development is carried out to form chamber patterns with photolithography. Next, lower plate material 50 is pitted to a predetermined depth to form the chamber parts using the developed film as a format. The technologies that are known to one skilled in the art, such as cutting or sandblasting can be used for forming the chamber parts. Finally, upper plate material 49, in which injection inlet 11 and air opening 12 are provided, is stacked over lower plate material 50.

EXAMPLE

Hereinafter, the present invention will be described specifically with reference to the example. This example is not limited to the present invention.

Example 1

Example 1 is the example corresponding to Embodiment 2. In Example 1, substrate 2 having flow path part 5 shown in FIGS. 5 to 8 (particularly FIG. 5) was made. An experiment of the behavior of stepwise liquid transfer was conducted for flow path part of Example 1.

Design of Liquid Transfer Substrate 2

Figure 12:
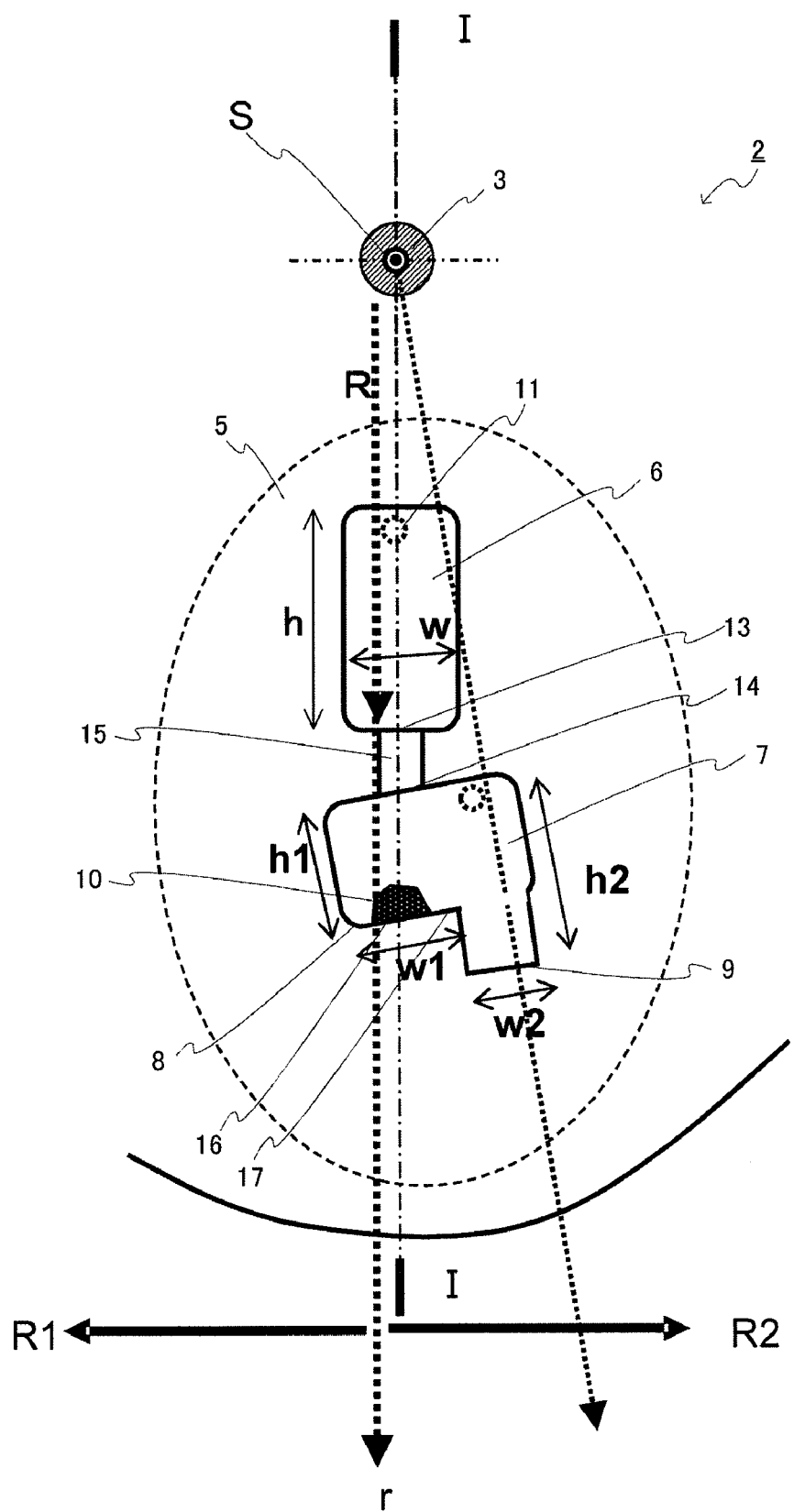
FIG. 12 is a plan view to explain design values of the substrate according to Example 1.

Flow path part 5 in substrate 2 shown in FIG. 12 was designed. The design values are shown in Table 1.

TABLE 1

| | Rotation radius R (mm) | Width w (mm) | Height h (mm) | Depth d (mm) |
|---|---|---|---|---|
| First chamber 6 #1 | 32 | w = 2 | h = 5 | 0.2 |
| Second chamber7 # First inner face | 36 | w1 = 1.8 | h1 = 3 | 0.4 |
| Second chamber 7 # Second inner face | 38 | w2 = 2 | h2 = 5 | 0.4 |
| Connecting part #c | — | 0.3 | — | 0.1 |

Substrate 2 was made based on the design values of Table 1, and a test was conducted to check the behavior of stepwise liquid transfer.

Production of Substrate 2

A negative thick film photoresist KMPR1030 (Nippon Kayaku Co., Ltd) was applied to a glass substrate subjected to cleaning treatment. KMPR 1030 is spin-coated with a spin-coater. A pre-rotation for ten seconds at 500 rpm, followed by main rotation for thirty seconds at 1000 rpm is performed. By changing the rotation speed of main rotation, it was possible to change the thickness of the coating film.

After that, the coating film was pre-baked for 20 minutes at 95° C., and was exposed via a mask in which flow paths and chambers were drawn. The intensity of exposure was approximately 1700 mJ/cm². Next, post exposure bake (PEB: Post Exposure Bake) was performed for 6 minutes at 95° C., development was carried out to form flow path and chamber patterns by photolithography. Next, the chamber parts in lower plate material 50 were formed by cutting. Finally, upper plate material 49, in which injection inlet 11 and air opening 12 were open, was stacked over lower plate material 50.

Stepwise Liquid Transfer Test

As sample solution (liquid 10), pure water or pure water containing blue pigment for increasing visibility was used. Sample solution of 1 μL; 0.5 μL; 0.2 μL were injected in first chamber 6 through injection inlet 11 in substrate 2 in Embodiment 1 with a Hamilton syringe. After that, substrate 2 was attached on liquid transfer apparatus 1 and was driven in rotation. The rotation speed was gradually increased by every 10 rpm/sec from 800 rpm.

Figure 13:
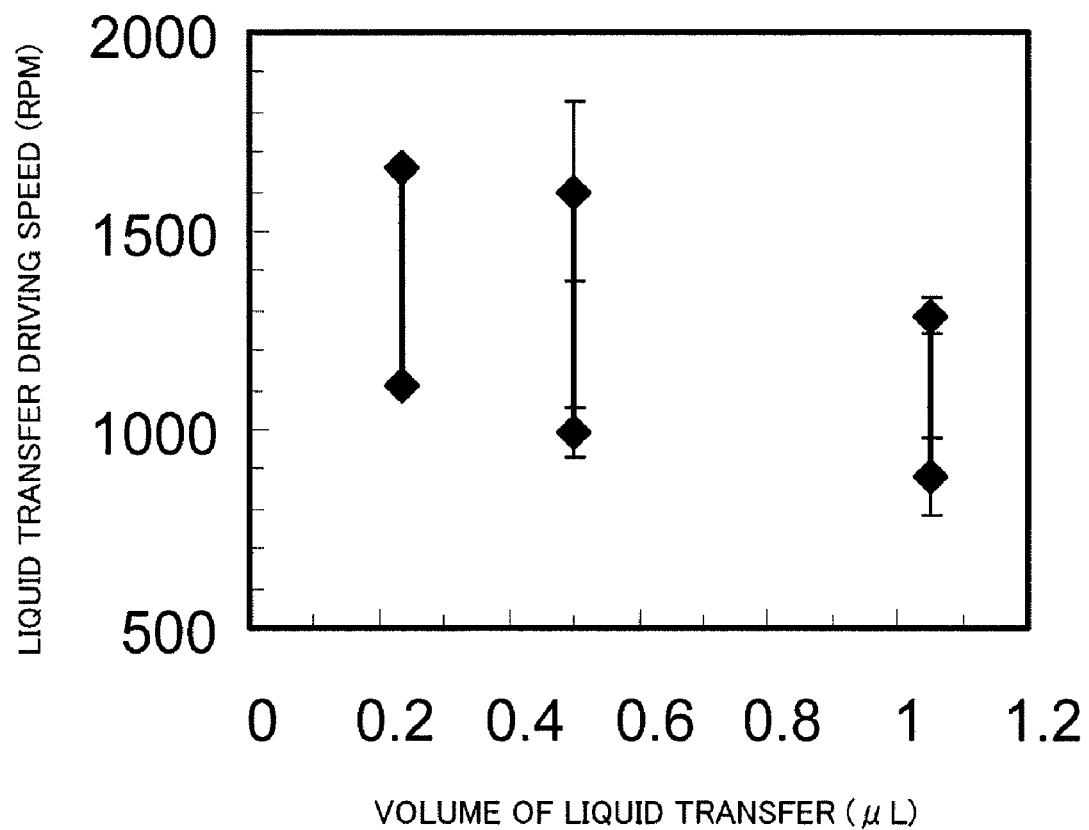
FIG. 13 is a graph showing the result of a multistage liquid transfer test in Example 1.

The rotation speed was found as the first rotation speed on which the solution was transferred from first chamber 6 to second chamber 7. The rotation speed was found as the second rotation speed on which the solution was transferred from the first inner face to the second inner face. The measurement was conducted three times for the same substrate 2. The average value of each measured rotation speed was shown in table 2 and FIG. 13.

| Amount of solution (μL) | First rotation speed $rpm_1$ (rpm) | Second rotation speed $rpm_2$ (rpm) |
| --- | --- | --- |
| 1 | 879 | 1286 |
| 0.5 | 993 | 1600 |
| 0.2 | 1108 | 1658 |

1 μL of solution injected in first chamber 6 was transferred from first chamber 6 to first inner face 8 of second chamber 7 at a rotation speed 879 rpm to become droplet, and did not flow in second inner face 9. The droplet retained on first inner face 8 of the retained area had an average width of 1.6 mm in a plan view. After that, the rotation speed is increased by 10 rpm/sec. The droplet spreads to the entire expansion area of the first inner face to reach the outermost periphery part at rotation speed 1286 rpm. The droplet had a width of 1.8 mm in a plan view. Then, the sample solution was transferred from first inner face 8 to second inner face 9.

With substrate 2 in which the 0.5 μL or 0.2 μL of solution was injected, similarly, the sample solution was transferred from first chamber 6 to second chamber 7, and, after the increase of rotation speed, the sample solution was transferred from first inner face 8 to second inner face 9.

0.5 μL of solution was transferred at 993 rpm from first chamber 6, and 0.2 μL of solution at 1108 rpm. The width of the droplet retained on the retaining area in first inner face 8 is 1.2 mm (0.5 μL solution) or 0.9 mm (0.2 μL solution) in a plan view, at the time point when the solution was transferred to second chamber 7. Further, 0.5 μL of sample solution was transferred from the first inner face to the second inner face in the second chamber at 1600 rpm, and 0.2 μL of sample solution at 1658 rpm. In this way, stepwise liquid transfer was checked experimentally.

The volume of the sample solution transferred to second inner face 9 was measured to find the proportion of the sample solution transferred to second inner face 9 with respect to the volume injected in first chamber 6. That is, "the proportion of transferred liquid" was measured. As a result, the proportion of transferred liquid was 96.9% when the amount of injected solution was 0.5 μL, and was 98.6% when the amount of injected solution was 0.2 μL. Loss of liquid during transfer was 3.1% and 1.4% of the amount of injection, respectively, which was very small. Therefore, almost the entire amount of injected liquid can be transferred, it is suitable for reducing the amount of liquid transfer.

The disclosure of Japanese Patent Application No. 2007-102090, filed on Apr. 9, 2007, including the specification, drawings and abstract, is incorporated herein by reference in its entirety.

INDUSTRIAL APPLICABILITY

The substrate and method for transferring liquid according to the present invention is suitable for use in devices for analyzing organizing material such as protein in biological sample (particularly, blood). Particularly, in analysis of a blood sample, after blood cells and plasmas are separated in a preparatory stage, protein contained in the separated plasmas may be targeted as a measurement target. Centrifugal separation is suitable for use in the separation. For that reason, it is possible to separate easily blood cells from plasmas for analyzing a blood sample in combination with a method of liquid transfer using a rotating substrate.

Further, by carrying reagents in chambers and conducting physical operation such as heating on chambers, it is possible to apply functions including reaction, purification and detection to the substrate. For this reason, the present invention is applicable for use in POCT (Point of care test) biosensors that separate, purify, react and detect protein and materials that serve as an indicator of health contained in a blood sample.

EXPLANATION OF REFERENCE NUMERALS

1 LIQUID TRANSFER APPARATUS
2 ROTATING SUBSTRATE
3 ROTATING AXIS
4 ROTATION DRIVE PART
5 PART
6 FIRST CHAMBER (SUPPLY SOURCE CHAMBER)
7 SECOND CHAMBER (SUPPLY DESTINATION CHAMBER)
8 FIRST INNER FACE
9 SECOND INNER FACE
10 LIQUID
11 INJECTION INLET
12 INJECTION INLET OR AIR OPENING
13 FIRST CONNECTING END PART (INPUT END PART)
14 SECOND CONNECTING END PART (OUTPUT END PART)
15 CONNECTING PART
16 RETAINING AREA
17 EXPANSION AREA
20 CONNECTING PART WIDTH
21 FIRST CHAMBER WIDTH
22 SECOND CHAMBER WIDTH
24 FIRST CHAMBER DEPTH
25 SECOND CHAMBER DEPTH
27 CONNECTING PART DEPTH
31 MOTOR
32 DRIVING CIRCUIT
33 CONTROL SIGNAL OUTPUT SECTION
34 SPEED CHARACTERISTIC APPLICATION PART
35 DRIVING SPEED DETECTOR
36 DRIVING SPEED CONTROLLING PART
41 UPPER PLATE MATERIAL
42 CONNECTING MEMBER
43 CHAMBER PLATE MATERIAL
44 LOWER PLATE MATERIAL
49 CHAMBER FORMING SUBSTRATE
50 LOWER PLATE MATERIAL
51 SUBSTRATE BODY
52 CHIP
53 ACCOMMODATING HOLE
R1 CLOCKWISE
R2 COUNTERCLOCKWISE
S AXIS OF ROTATION (AXIS)
R Radial Direction
R1D RADIUS OF ROTATION OF FIRST CHAMBER
R1U ROTATION RADIUS OF IMAGINARY LIQUID SURFACE OF FIRST CHAMBER
R2D ROTATION RADIUS OF FIRST INNER FACE IN SECOND CHAMBER
R2U ROTATION RADIUS OF IMAGINARY LIQUID SURFACE ON FIRST INNER FACE IN SECOND CHAMBER
R3D ROTATION RADIUS OF IMAGINARY LIQUID SURFACE ON SECOND INNER FACE IN SECOND CHAMBER FC₁ FIRST CAPILLARY FORCE
FC₂ SECOND CAPILLARY FORCE
PC₁ FIRST CAPILLARY PRESSURE
PC₂ SECOND CAPILLARY PRESSURE
FG₁ FIRST CENTRIFUGAL FORCE
FG₂ SECOND CENTRIFUGAL FORCE
PG₁ FIRST CENTRIFUGAL PRESSURE
PG₂ SECOND CENTRIFUGAL PRESSURE
$T_1$ to $T_N$ SURFACE TENSIONS IN ALL DIRECTIONS
$\theta_C$ CONTACT ANGLE

The invention claimed is:

1. A substrate that is rotatable about a rotating axis and that has a flow path part including a chamber formed inside the substrate, wherein:
   an interior wall of the chamber, which is configured to generate no capillary force, comprises:
   a first inner face that has a plane intersecting with a centrifugal direction being a line running orthogonal to the rotating axis of the substrate from the rotating axis; and
   a second inner face that has a plane which is placed in a location farther from the rotating axis than the first inner face and which is intersecting with the centrifugal direction being a line running orthogonal to the rotating axis of the substrate from the rotating axis;
   wherein the first inner face has an area on which a droplet of liquid supplied is retained, and has an area that allows expansion of a contact area of the retained droplet by rotation of the substrate and communicates with the second inner face.

2. The substrate according to claim 1, wherein the area on which the droplet is retained is hydrophobic.

3. The substrate according to claim 1, further comprising a member of a central shaft that works as the rotating axis.

4. A substrate that is rotatable about a rotating axis and that has a flow path part formed inside the substrate, wherein:
   the flow path part comprises:
   a first chamber;
   a second chamber that is placed in a location farther from the rotating axis than the first chamber; and
   a connecting part that connects the first chamber and the second chamber;
   wherein the first chamber is provided with an injection inlet via which provides access from outside the substrate; and
   an interior wall of the second chamber, which is configured to generate no capillary force, comprises:
   a first inner face that has a plane intersecting with a centrifugal direction being a line running orthogonal to the rotating axis of the substrate from the rotating axis; and
   a second inner face that has a plane which is placed in a location farther from the rotating axis than the first inner face and which is intersecting with the centrifugal direction being a line running orthogonal to the rotating axis of the substrate from the rotating axis; and
   the first inner face has an area on which a droplet of liquid supplied is retained, and has an area that allows expansion of a contact area of the retained droplet by rotation of the substrate and that communicates with the second inner face.

5. A method of transferring liquid in a chamber formed inside the substrate according to claim 1, comprising:
   retaining a droplet of liquid on the retaining area in the first inner face; and
   transferring the liquid to the second inner face such that the substrate rotates about the rotating axis to spread the contact area of the retained droplet of liquid.

6. A method of transferring liquid in the second chamber formed inside the substrate according to claim 4, comprising:
   retaining a droplet of liquid in the area of the first inner face such that the substrate rotates about the rotating axis at a first rotation speed, to allow the liquid injected in the first chamber to flow in the second chamber; and
   transferring the liquid to a second inner face such that the substrate rotates about the rotating axis at a second rotation speed that is faster than the first rotation speed, to spread the contact area of the retained droplet of liquid.

7. A liquid transfer apparatus comprising:
   the substrate according to claim 1; and
   a rotation drive part that moves the substrate around a center of rotation.

8. The liquid transfer apparatus according to claim 7, wherein the rotation drive part comprises:
   a motor that rotates the substrate around the center of rotation; and
   a speed controller that is configured to control a rotation speed of the motor.

9. The liquid transfer apparatus according to claim 8, wherein the rotation drive part further comprises:
   a driving speed detector that detects a rotation speed of the substrate during rotation; and
   a driving speed controller that corrects a speed characteristic, which is given to the motor by a speed characteristic application part, based on the rotation speed detected by the driving speed detector.

* * * * *